United States Patent
Schwarz et al.

(10) Patent No.: US 6,627,200 B1
(45) Date of Patent: Sep. 30, 2003

(54) UTILIZATION OF CD 137 IN ORDER TO PROMOTE THE PROLIFERATION OF PERIPHERAL MONOCYTES

(75) Inventors: Herbert Schwarz, Theuern (DE); Joachim Langstein, Regensburg (DE)

(73) Assignee: Merckle GmbH (DE)

( * ) Notice: Subject to any disclaimer, the term of this patent is extended or adjusted under 35 U.S.C. 154(b) by 0 days.

(21) Appl. No.: 09/623,545

(22) PCT Filed: Mar. 5, 1999

(86) PCT No.: PCT/EP99/01440

§ 371 (c)(1),
(2), (4) Date: Nov. 30, 2000

(87) PCT Pub. No.: WO99/44629

PCT Pub. Date: Sep. 10, 1999

(51) Int. Cl.[7] ............................................... A61K 38/18

(52) U.S. Cl. .............................. 424/195.11; 424/185.1; 424/193.1; 530/350; 536/23.5; 514/12

(58) Field of Search ......................... 530/350; 536/23.5; 514/12; 424/185.1, 193.1, 195.11

(56) References Cited

U.S. PATENT DOCUMENTS

| | | | | |
|---|---|---|---|---|
| 5,674,704 A | * | 10/1997 | Goodwin et al. | 435/320.1 |
| 5,679,704 A | | 10/1997 | Schönafinger et al. | |

FOREIGN PATENT DOCUMENTS

| | | | | |
|---|---|---|---|---|
| CA | 2108401 A1 | * | 10/1993 | |
| WO | WO 9426290 A1 | * | 11/1994 | A61K/37/02 |
| WO | WO 9507984 A1 | * | 3/1995 | C12N/15/12 |

OTHER PUBLICATIONS

Alderson, Mark R. et al., "Molecular and Biological Characterization of Human 4–1BB and Its Ligand," *Eur. J Immunology*, 1994. 24:2219–2227. (Exhibit 1).

Armitage, Richard J., "Tumor Necrosis Factor Receptor Superfamily Members and Their Ligands," *Current Opinion in Immunology*, 1994, 6:407–413 . . . (Exhibit 2).

DeBenedette, Mark A. et al., "Role of 4–1BB Ligand in Constimulation of T Lymphocyte Growth and its Upregulation on M12 B Lymphomas by cAMP," *J. Exp. Med.*, Mar. 1995, 181:985–992. . . (Exhibit 3).

Gruss, Hans–Jurgen et al., "Tumor Necrosis Factor Ligand Superfamily: Involvement in the Pathology of Malignant Lymphomas," *Blood*, vol. 85, No. 12 (Jun. 15), 1995:pp 3378–3404. (Exhibit 4).

Hurtado, Jose' C. et al., "Potential Role of 4–1BB in T Cell Activation: Comparison with the Costimulatory Molecule CD28[1]," *The Journal of Immunology*, 1995, 155:3360–3367. (Exhibit 5).

Kim, Young–June et al., "Novel T Cell Antigen 4–1BB Associates with the Protein Tyrosine Kinase p56[lck1]," *The Journal of Immunology*, Aug. 1, 1993, 151:1255–1262. (Exhibit 6).

Kooten, Cees Van et al., "CD40–CD40 Ligand: A Multifunctional Receptor–Ligand Pair," *Advances in Immunology*, 1996, 61:1–77. (Exhibit 7).

Kwon, Byoung S. et al., "cDNA Sequences of Two Inducible T–Cell Genes," *Proc. Natl. Acad. Sci. USA*: Mar. 1989, 86:1963–1967, Immunology (Exhibit 8).

Pollok, Karen E. et al., "Inducible T Cell Antigen 4–1BB[1]: Analysis of Expression and Function," *The Journal of Immunology*, 1993 150–771. (Exhibit 9).

Schwarz, Herbert et al., "ILA, the Human 4–1BB Homologue, Is Inducible in Lymphoid and Other Cell Lineages," *Blood*, vol. 85, No. 4 (Feb. 15), 1995: pp. 1043–1052 (Exhibit 10).

Anderson, R. et al. 1990 *J. Leu Biol*.47:490–497. (Exhibit 12).

Behr, J.P. et al., (1989) *Proc. Natl. Acad. Sci USA* 86:6982–6986. (Exhibit 13).

Bratton, D.L., et al., 1995 *J Clin Invest* 95:211–218. (Exhibit 14).

Contreras, T.J. et al., 1980 *Cell Immunol.*, 54(1):215–229. (Exhibit 15).

Elner, S.G., 1995 *Curr Eye Res* 14:1045–1053. (Exhibit 16).

Felger, J.H. et al., 1994 *J. Biol. Chem.* 269: 2550–2561. (Exhibit 17).

Gao, X. & Huang, L. 1991 *Biochem Biophys Res. Commun.* 179:280–285. (Exhibit 18).

Kawano, Y., 1995 *Eur. J. Haematol.* 54:147–152. (Exhibit 19).

Langstein, J. et al., 1998 *J. Immunol* 160:2488–2494. (Exhibit 20).

Michel, J., et al., 1998 *Eur J Immunol* 28:290–295. (Exhibit 21).

Meyskens, F.L., et al., 1979 *Exp Haematol.*, 7(8):401–410. (Exhibit 22).

Pastan, et al., 1986 *Cell*, 47:641–648. (Exhibit 23).

Saunders, M.A., 1997 *Br. J. Pharmacol* 120:545–546. (Exhibit 24).

Schwarz, H. et al., , 1996 *Blood* 87(7): 2839–2845. (Exhibit 25).

Schwarz, H. et al., 1993 *Gene* 134:295–298. (Exhibit 26).

Schwarz, H. et al., 1997 *Biochem Biophys Res Com* 235:699–703. (Exhibit 27).

Thorpe et al., 1987 *Cancer Res.* 47:5924–5931. (Exhibit 28).

van Furth, R., et al., 1979 *Blood* 54:485–500. (Exhibit 29).

Vitetta, et al., 1987 *Science* 238:10981104. (Exhibit 30).

Weiner, R.S. et al., 1980 *J. Immunol. Methods*, 36(2):89–97. (Exhibit 31).

Xing, Z., et al., 1992 *Am J Respir Cell Mol Boil* 6:212–218. (Exhibit 32).

Young, D.A., 1990 *J Immunol* 145:607–615. (Exhibit 33).

Zhou, X. & Huang, L. (1994) *Biochem. Biophys. Acta* 1189, 195–203. (Exhibit 34).

* cited by examiner

Primary Examiner—Yvonne Eyler
Assistant Examiner—Eileen B. O'Hara
(74) Attorney, Agent, or Firm—Mandel & Adriano

(57) ABSTRACT

The invention relates to the utilization of monocytes growth factor CD137 or of a functional analogue thereof in order to produce a medicament for promoting the proliferation of peripheral monocytes of a mammal. The invention especially relates to the utilization of the growth factor for treating pathological conditions.

32 Claims, 18 Drawing Sheets

FIG. 1A1

```
-139                                                    CCACGCGTCCGAG
-126 ACCAAGGAGTGGAAAGTTCTCCGGCAGCCCTGAGATCTCAAGAGTGACATTTGTGAGACCAGC
-63  TAATTTGATTAAAATTCTCTTGGAATCAGCTTTGCTAGTATCATACCTGTGCCAGATTTCATC

1  ATG GGA AAC AGC TGT TAC AAC ATA GTA GCC ACT CTG TTG CTG GTC CTC
  1  Met Gly Asn Ser Cys Tyr Asn Ile Val Ala Thr Leu Leu Leu Val Leu

49  AAC TTT GAG AGG ACA AGA TCA TTG CAG GAT CCT TGT AGT AAC TGC CCA
 17  Asn Phe Glu Arg Thr Arg Ser Leu Gln Asp Pro Cys Ser Asn Cys Pro

97  GCT GGT ACA TTC TGT GAT AAT AAC AGG AAT CAG ATT TGC AGT CCC TGT
 33  Ala Gly Thr Phe Cys Asp Asn Asn Arg Asn Gln Ile Cys Ser Pro Cys

145  CCT CCA AAT AGT TTC TCC AGC GCA GGT GGA CAA AGG ACC TGT GAC ATA
 49  Pro Pro Asn Ser Phe Ser Ser Ala Gly Gly Gln Arg Thr Cys Asp Ile

193  TGC AGG CAG TGT AAA GGT GTT TTC AGG ACC AGG AAG GAG TGT TCC TCC
 65  Cys Arg Gln Cys Lys Gly Val Phe Arg Thr Arg Lys Glu Cys Ser Ser

241  ACC AGC AAT GCA GAG TGT GAC TGC ACT CCA GGG TTT CAC TGC CTG GGG
 81  Thr Ser Asn Ala Glu Cys Asp Cys Thr Pro Gly Phe His Cys Leu Gly

289  GCA GGA TGC AGC ATG TGT GAA CAG GAT TGT AAA CAA GGT CAA GAA CTG
 97  Ala Gly Cys Ser Met Cys Glu Gln Asp Cys Lys Gln Gly Gln Glu Leu

337  ACA AAA AAA GGT TGT AAA GAC TGT TGC TTT GGG ACA TTT AAC GAT CAG
113  Thr Lys Lys Gly Cys Lys Asp Cys Cys Phe Gly Thr Phe Asn Asp Gln

385  AAA CGT GGC ATC TGT CGA CCC TGG ACA AAC TGT TCT TTG GAT GGA AAG
129  Lys Arg Gly Ile Cys Arg Pro Trp Thr Asn Cys Ser Leu Asp Gly Lys
                                          *
433  TCT GTG CTT GTG AAT GGG ACG AAG GAG AGG GAC GTG GTC TGT GGA CCA
145  Ser Val Leu Val Asn Gly Thr Lys Glu Arg Asp Val Val Cys Gly Pro
                     *
481  TCT CCA GCC GAC CTC TCT CCG GGA GCA TCC TCT GTG ACC CCG CCT GCC
161  Ser Pro Ala Asp Leu Ser Pro Gly Ala Ser Ser Val Thr Pro Pro Ala

529  CCT GCG AGA GAG CCA GGA CAC TCT CCG CAG ATC ATC TCC TTC TTT CTT
177  Pro Ala Arg Glu Pro Gly His Ser Pro Gln Ile Ile Ser Phe Phe Leu

577  GCG CTG ACG TCG ACT GCG TTG CTC TTC CTG CTG TTC TTC CTC ACG CTC
193  Ala Leu Thr Ser Thr Ala Leu Leu Phe Leu Leu Phe Phe Leu Thr Leu

625  CGT TTC TCT GTT GTT AAA CGG GGC AGA AAG AAA CTC CTG TAT ATA TTC
209  Arg Phe Ser Val Val Lys Arg Gly Arg Lys Lys Leu Leu Tyr Ile Phe

673  AAA CAA CCA TTT ATG AGA CCA GTA CAA ACT ACT CAA GAG GAA GAT GGC
225  Lys Gln Pro Phe Met Arg Pro Val Gln Thr Thr Gln Glu Glu Asp Gly
                                                 CKII
721  TGT AGC TGC CGA TTT CCA GAA GAA GAA GAA GGA GGA TGT GAA CTG TGA
241  Cys Ser Cys Arg Phe Pro Glu Glu Glu Glu Gly Gly Cys Glu Leu ---
          PKC
```

FIG. 1A2

```
 769 AATGGAAGTCAATAGGGCTGTTGGGACTTTCTTGAAAAGAAGCAAGGAAATATGAGTCATCCGC
 833 TATCACAGCTTTCAAAAGCAAGAACACCATCCTACATAATACCCAGGATTCCCCCAACACACGT
 897 TCTTTTCTAAATGCCAATGAGTTGGCCTTTAAAAATGCACCACTTTTTTTTTTTTTTTGGACAG
 961 GGTCTCACTCTGTCACCCAGGCTGGAGTGCAGTGGCACCACCATGGCTCTCTGCAGCCTTGACC
1024 TCTGGGAGCTCAAGTGATCCTCCTGCCTCAGTCTCCTGAGTAGCTGGAACTACAAGGAAGGGCC
1089 ACCACACCTGACTAACTTTTTTGTTTTTTGTTGGTAAAGATGGCATTTCGCCATGTTGTACAGG
1153 CTGGTCTCAAACTCCTAGGTTCACTTTGGCCTCCCAAAGTGCTGGGATTACAGACATGAACTGC
1217 CAGGCCCGGCCAAAATAATGCACCACTTTTAACAGAACAGACAGATGAGGACAGAGCTGGTGA
1281 T(A)20
```

FIG. 1B

```
huCD137    1 MGNSCYNIVATLLLVLNFERTRSLQDPCSNCPAGTFCDNNRNQICSPCPP  50
             ||.|||:|..:||::  |:..:|::.|..||..:|||| . !.:|..|||
muCD137    1 MGNNCYNVVIVLLLVGCEKVGAVQNSCDNCQPGTFCRKY.NPVCKSCPP   49 huCD137   51 NSFSSAGGQRTCDICRQCKGVFRTRKECSTSNAECDCTPGFHCLGAGCS  100
             ..|||  |||..|:|||   |  |:  |||  |||| |||::|::.|.
muCD137   50 STFSSIGGQPNCNICRVCAGYFRFKKFCSSTHNAECBCIBGFHCLGPQCT  99 huCD137  101 MCEQDCRQGQELTKKGCKDCCFGTFNDQK.RGICRPWTNCSLDGKSVLVN 149
             .||.|||.|||||||||:||.|||.|:::||||| |:|||||||||||.|||
muCD137  100 RCEKDCRPGQELTKQGCKTCSLGTFNDQNGTVCRPWTNCSLDGRSVLKT  149 huCD137  150 GTKERDVVCGPSPADLSPGAS.SVTPPAPAREFGHSPQIISFFLALTSTA 198
             ||.||||||||.....:||.. ||||.:.: .||| |::. :|||||| !
muCD137  150 GTTERDVVCGPPVVSFSPSTTISVTPBGGP..GGHSLQVLTLFLALTS.A 196 huCD137  199 LLFLFFLFLTLRFSVVKRGRKKLLYIFKQPFMRPVQTTQEEDGCSCRFPEE 248
             ||: |:||:|| |||:||  |||  |||  .||||||:.... |||||| |:|
muCD137  197 LLLALIFITLLPSVLKWIRKPFHIFKQPFKTTGAAQEEDACSCRCPQE   246 huCD137  249 EEGG...CEL  255
             ||||   ||
muCD137  247 EEGGGGGYEL  256
```

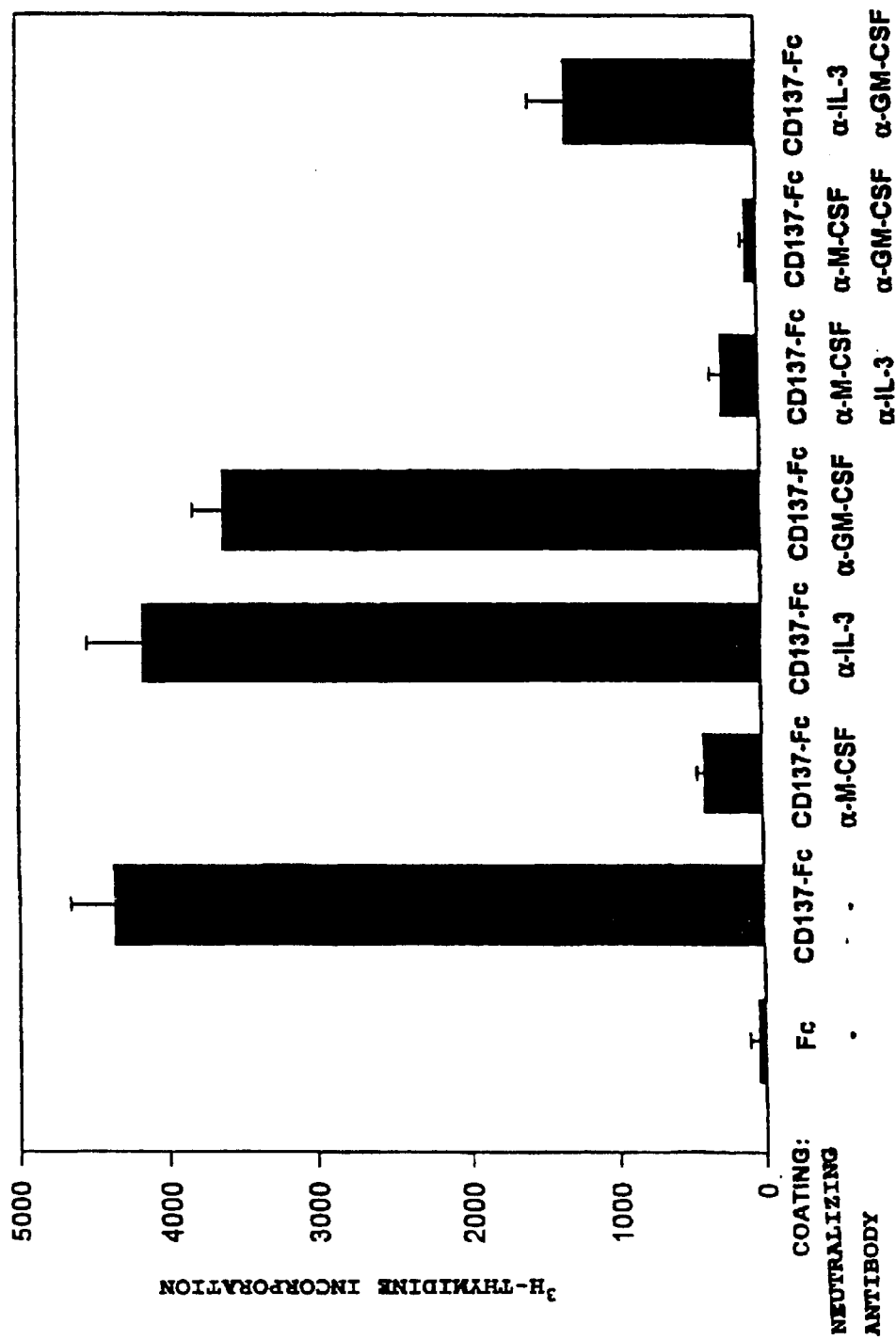

SEQUENCE LISTING

<160> NUMBER OF SEQ ID NOS: 3

<210> SEQ ID NO 1
<211> LENGTH: 1439
<212> TYPE: DNA
<213> ORGANISM: Homo sapiens
<220> FEATURE:
<221> NAME/KEY: CDS
<222> LOCATION: (140)..(904)

<400> SEQUENCE: 1

```
ccacgcgtcc gagaccaagg agtggaaagt tctccggcag ccctgagatc tcaagagtga      60
catttgtgag accagctaat ttgattaaaa ttctcttgga atcagctttg ctagtatcat     120
acctgtcgca gatttcatc atg gga aac agc tgt tac aac ata gta gcc act     172
                      Met Gly Asn Ser Cys Tyr Asn Ile Val Ala Thr
                        1               5                  10
```

-continued

| | | |
|---|---|---|
| ctg ttg ctg gtc ctc aac ttt gag agg aca aga tca ttg cag gat cct<br>Leu Leu Leu Val Leu Asn Phe Glu Arg Thr Arg Ser Leu Gln Asp Pro<br>              15                    20               25 | 220 |
| tgt agt aac tgc cca gct ggt aca ttc tgt gat aat aac agg aat cag<br>Cys Ser Asn Cys Pro Ala Gly Thr Phe Cys Asp Asn Asn Arg Asn Gln<br>        30                    35                   40 | 268 |
| att tgc agt ccc tgt cct cca aat agt ttc tcc agc gca ggt gga caa<br>Ile Cys Ser Pro Cys Pro Pro Asn Ser Phe Ser Ser Ala Gly Gly Gln<br>45                    50                    55 | 316 |
| agg acc tgt gac ata tgc agg cag tgt aaa ggt gtt ttc agg acc agg<br>Arg Thr Cys Asp Ile Cys Arg Gln Cys Lys Gly Val Phe Arg Thr Arg<br>60                    65                    70               75 | 364 |
| aag gag tgt tcc tcc acc agc aat gca gag tgt gac tgc act cca ggg<br>Lys Glu Cys Ser Ser Thr Ser Asn Ala Glu Cys Asp Cys Thr Pro Gly<br>              80                    85                   90 | 412 |
| ttt cac tgc ctg ggg gca gga tgc agc atg tgt gaa cag gat tgt aaa<br>Phe His Cys Leu Gly Ala Gly Cys Ser Met Cys Glu Gln Asp Cys Lys<br>              95                   100               105 | 460 |
| caa ggt caa gaa ctg aca aaa aaa ggt tgt aaa gac tgt tgc ttt ggg<br>Gln Gly Gln Glu Leu Thr Lys Lys Gly Cys Lys Asp Cys Cys Phe Gly<br>        110                   115               120 | 508 |
| aca ttt aac gat cag aaa cgt ggc atc tgt cga ccc tgg aca aac tgt<br>Thr Phe Asn Asp Gln Lys Arg Gly Ile Cys Arg Pro Trp Thr Asn Cys<br>125                  130               135 | 556 |
| tct ttg gat gga aag tct gtg ctt gtg aat ggg acg aag gag agg gac<br>Ser Leu Asp Gly Lys Ser Val Leu Val Asn Gly Thr Lys Glu Arg Asp<br>140                  145               150               155 | 604 |
| gtg gtc tgt gga cca tct cca gcc gac ctc tct ccg gga gca tcc tct<br>Val Val Cys Gly Pro Ser Pro Ala Asp Leu Ser Pro Gly Ala Ser Ser<br>               160                     165               170 | 652 |
| gtg acc ccg cct gcc cct gcg aga gag cca gga cac tct ccg cag atc<br>Val Thr Pro Pro Ala Pro Ala Arg Glu Pro Gly His Ser Pro Gln Ile<br>              175                     180               185 | 700 |
| atc tcc ttc ttt ctt gcg ctg acg tcg act gcg ttg ctc ttc ctg ctg<br>Ile Ser Phe Phe Leu Ala Leu Thr Ser Thr Ala Leu Leu Phe Leu Leu<br>              190                     195               200 | 748 |
| ttc ttc ctc acg ctc cgt ttc tct gtt gtt aaa cgg ggc aga aag aaa<br>Phe Phe Leu Thr Leu Arg Phe Ser Val Val Lys Arg Gly Arg Lys Lys<br>205                  210               215 | 796 |
| ctc ctg tat ata ttc aaa caa cca ttt atg aga cca gta caa act act<br>Leu Leu Tyr Ile Phe Lys Gln Pro Phe Met Arg Pro Val Gln Thr Thr<br>220                  225               230               235 | 844 |
| caa gag gaa gat ggc tgt agc tgc cga ttt cca gaa gaa gaa gga<br>Gln Glu Glu Asp Gly Cys Ser Cys Arg Phe Pro Glu Glu Glu Glu Gly<br>              240                     245               250 | 892 |
| gga tgt gaa ctg tgaaatggaa gtcaataggg ctgttgggac tttcttgaaa<br>Gly Cys Glu Leu<br>              255 | 944 |
| agaagcaagg aaatatgagt catccgctat cacagctttc aaaagcaaga acaccatcct | 1004 |
| acataatacc caggattccc ccaacacacg ttcttttcta aatgccaatg agttggcctt | 1064 |
| taaaaatgca ccactttttt ttttttttg gacagggtct cactctgtca cccaggctgg | 1124 |
| agtgcagtgg caccaccatg gctctctgca gccttgacct ctgggagctc aagtgatcct | 1184 |
| cctgcctcag tctcctgagt agctggaact acaaggaagg gccaccacac ctgactaact | 1244 |
| tttttgtttt ttgttggtaa agatggcatt tcgccatgtt gtacaggctg gtctcaaact | 1304 |
| cctaggttca ctttggcctc ccaaagtgct gggattacag acatgaactg ccaggcccgg | 1364 |
| ccaaaataat gcaccacttt taacagaaca gacagatgag gacagagctg gtgataaaaa | 1424 | aaaaaaaaaa aaaaa                                                    1439

<210> SEQ ID NO 2
<211> LENGTH: 255
<212> TYPE: PRT
<213> ORGANISM: Homo sapiens

<400> SEQUENCE: 2

```
Met Gly Asn Ser Cys Tyr Asn Ile Val Ala Thr Leu Leu Leu Val Leu
  1               5                  10                  15

Asn Phe Glu Arg Thr Arg Ser Leu Gln Asp Pro Cys Ser Asn Cys Pro
             20                  25                  30

Ala Gly Thr Phe Cys Asp Asn Asn Arg Asn Gln Ile Cys Ser Pro Cys
         35                  40                  45

Pro Pro Asn Ser Phe Ser Ser Ala Gly Gly Gln Arg Thr Cys Asp Ile
     50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 3
<211> LENGTH: 256
<212> TYPE: PRT
<213> ORGANISM: Mus musculus

<400> SEQUENCE: 3

```
Met Gly Asn Asn Cys Tyr Asn Val Val Val Ile Val Leu Leu Leu Val
  1               5                  10                  15

Gly Cys Glu Lys Val Gly Ala Val Gln Asn Ser Cys Asp Asn Cys Gln
             20                  25                  30

Pro Gly Thr Phe Cys Arg Lys Tyr Asn Pro Val Cys Lys Ser Cys Pro
         35                  40                  45

Pro Ser Thr Phe Ser Ser Ile Gly Gly Gln Pro Asn Cys Asn Ile Cys
     50                  55                  60
```

```
-continued

Arg Val Cys Ala Gly Tyr Phe Arg Phe Lys Lys Phe Cys Ser Ser Thr
 65              70              75              80

His Asn Ala Glu Cys Glu Cys Ile Glu Gly Phe His Cys Leu Gly Pro
             85              90              95

Gln Cys Thr Arg Cys Glu Lys Asp Cys Arg Pro Gly Gln Glu Leu Thr
            100             105             110

Lys Gln Gly Cys Lys Thr Cys Ser Leu Gly Thr Phe Asn Asp Gln Asn
        115             120             125

Gly Thr Gly Val Cys Arg Pro Trp Thr Asn Cys Ser Leu Asp Gly Arg
    130             135             140

Ser Val Leu Lys Thr Gly Thr Thr Glu Lys Asp Val Val Cys Gly Pro
145             150             155             160

Pro Val Val Ser Phe Ser Pro Ser Thr Thr Ile Ser Val Thr Pro Glu
                165             170             175

Gly Gly Pro Gly Gly His Ser Leu Gln Val Leu Thr Leu Phe Leu Ala
            180             185             190

Leu Thr Ser Ala Leu Leu Leu Ala Leu Ile Phe Ile Thr Leu Leu Phe
        195             200             205

Ser Val Leu Lys Trp Ile Arg Lys Lys Phe Pro His Ile Phe Lys Gln
    210             215             220

Pro Phe Lys Lys Thr Thr Gly Ala Ala Gln Glu Glu Asp Ala Cys Ser
225             230             235             240

Cys Arg Cys Pro Gln Glu Glu Glu Gly Gly Gly Gly Gly Tyr Glu Leu
                245             250             255
```

UTILIZATION OF CD 137 IN ORDER TO PROMOTE THE PROLIFERATION OF PERIPHERAL MONOCYTES

The present invention relates to the use of the monocyte growth factor CD137 for promoting the proliferation of peripheral monocytes and in particular the use of CD137 for the treatment of various disease states which are treatable in a novel manner by means of the proliferation-promoting action of CD137.

Peripheral monocytes of the blood and the macrophages originating from them from body cavities and tissues are a constituent of the mononuclear phagocytic system of the body. In particular, monocytes and macrophages are effector cells of the non-specific immune defence system of the body. Monocytes develop over a number of intermediate stages from the haematopoietic stem cells in the bone marrow. They circulate over a period of time of approximately 20 to 30 hours in the blood. From there, they migrate into the various organs and tissue systems and there develop to site-specific macrophages. Here, the surrounding tissue has a formative influence on them and they develop additional functions. A differentiation is therefore made according to tissue type, for example macrophages of the lung (alveolar macrophages), of the abdominal cavity (peritoneal macrophages), of the spleen (splenic macrophages), of the liver (Kupffer cells), of the joints, of the bone (osteoclasts), of the connective tissue, of the brain and of the kidney.

Monocytes and macrophages have a central position in the context of the inflammatory reactions occurring in the body. In non-inflamed tissue, the object of macrophages is the elimination of old cells. Moreover, they produce a large number of soluble factors which are important for communication within the immune system. If the cells are involved, however, in an inflammatory process, they are in an activated state with greatly modified phenotypical and functional properties. In this case, they exert important effector functions influencing the course of the disease. These include phagocytosis and intracellular destruction of microorganisms, immune complexes and damaged cells, but also the antibody-dependent and -independent cytotoxicity reactions against tumour cells, parasites and virus-infected cells. Moreover, monocytes and macrophages are of central importance in the induction and regulation of the immune response. Namely, they are moreover secretory highly active cells, which affect the immune response by means of the increased release of cytokines.

CD137 is a member of the tumour necrosis factor receptor families and is moreover known (Kwon, B. S., et al., Proc Natl Acad Sci USA 86:1963, 1989; Schwarz H. et al., Gene 134:295,1993; Alderson, M. R., et al., Eur J Immunol 24:2219,1994) under the names ILA or 4-1BB (homologues from the mouse). CD137 is expressed by activated lymphocytes and monocytes, the expression by primary cells being dependent on activation (Schwarz H. et al., Blood 85:1043, 1995). The CD137 expression is rapidly inducible, for example, by activation of T lymphocytes with phytohaemagglutin in (PHA) or phorbol-12-myristate-13-acetate (PMA). In monocytes, CD137 is inducible by activation with lipopolysaccharide (LPS), IL-1β and PMA. In B lymphocytes, CD137 expression is induced by antibodies against cell-surface immunoglobulin or TMA, and by transformation with EBV (Epstein-Barr virus). In non-lymphoid cells (such as, in particular, chondrocytes), CD137 is strongly inducible by the proinflammatory cytokine IL-1β. Soluble forms of CD137 are produced by differential splicing and can be detected in raised concentrations in sera of patients with rheumatoid arthritis (Michel, J., et al., Eur J Immunol 28:290, 1998). The gene for human CD137 is on chromosome 1p36 in a cluster of related genes (Schwarz, H., et al., Biochem Biophys Res Com 235:699, 1997).

It is moreover known of recombinant CD137 protein that in immobilized form it brings about an activation of monocytes. The results of the activation is an increased expression of pro-inflammatory cytokines, an inhibition of the anti-inflammatory cytokine IL-10 and the induction of activation markers, such as ICAM (Langstein J. et al., J. Immunol 160–2488, 1998). A life-prolonging or proliferation-promoting action on monocytes is not described therein.

As already mentioned above, monocytes have a key function in the context of the immune response, and are of essential importance for the production of benign immune reactions against tumours and pathogens. Attracted by signals, such as, for example, from cytokines, they migrate from the blood circulation to the site of the inflammation. An accumulation of monocytes and macrophages is a characteristic feature of chronic inflammations. This accumulation is further promoted by cytokines, which are released at the site of inflammation, such as, for example, macrophage colony-stimulating factor (M-CSF), granulocyte-macrophage colony-stimulating factor (GM-CSF) and interleukin 3 (IL-3), which have a favorable effect on the survival of monocytes and macrophages (Young, D. A., J Immunol 145:607, 1990; Xing, Z., et al., Am J Respir Cell Mol Biol 6:212, 1992; Bratton, D. L., et al., J Clin Invest 95:211, 1995).

Until now, it was assumed of peripheral monocytes and macrophages that they are not capable of proliferation, i.e. of replication (cf. Xing, Z. et al., Supra; van Furth, R., et al., Blood 54–485, 1979).

From the above details, it is evident that the treatment of numerous disorders, such as, for example, tumours, infections by bacteria, fungi or viruses, could be markedly improved if an increased phagocytosis and intracellular destruction of microorganisms, immune complexes and damaged cells, and also an improved anti-body-dependent or -independent cytotoxicity reaction against tumour cells, microorganisms and cells infected thereby could be produced by replication of the monocytes/macrophages.

It is moreover known that various therapeutic forms of treatment, such as, for example, the chemotherapy or radiation therapy of cancer patients, and the administration of immunosuppressants, drastically reduces the number of monocytes and macrophages. After completion of therapeutic procedures of this type, it is as a rule desirable to increase the number of monocytes/macrophages again to values in the normal range and consequently to stabilize the immune system of the patient again.

It is therefore the object of the present invention to make available a route which makes it possible to specifically increase the number of peripheral monocytes and consequently the number of macrophages, in order to make possible an improved treatment of disease states which are associated with an inadequate number of active monocytes/macrophages.

It was surprisingly possible to achieve this object starting from the finding that the cell-surface protein CD137, which is known per se, and functional analogues thereof, contrary to previous assumptions, induces the proliferation of peripheral monocytes independently of the haematopoietic stem cells. This surprisingly opens up a large number of new therapeutic application possibilities for CD137.

Specific embodiments of the present invention are illustrated in greater detail below with reference to the accompanying figures. In these:

FIG. 1 (A1 and A2) shows the cDNA sequence (SEQ ID NO: 1) and the amino acid sequence (SEQ ID NO: 2) of human CD137 derived therefrom. Signal peptide (position +1 to +17) and transmembrane domain (position +187 to 213) are underlined in each case. Potential glycosylation sites are marked by asterisks; potential phosphorylation sites (position +242 for protein kinase C; positions +234 and +235 for casein kinase II are also indicated) the polyadenylation signal is shown in bold; (B) an alignment of the amino acid sequences of human (SEQ ID NO: 2) and murine CD137 (SEQ ID NO: 3); identical amino acids are shown by vertical lines; amino acids with high, low or no similarity are marked by a colon, full stop or blank.

Figure 2:
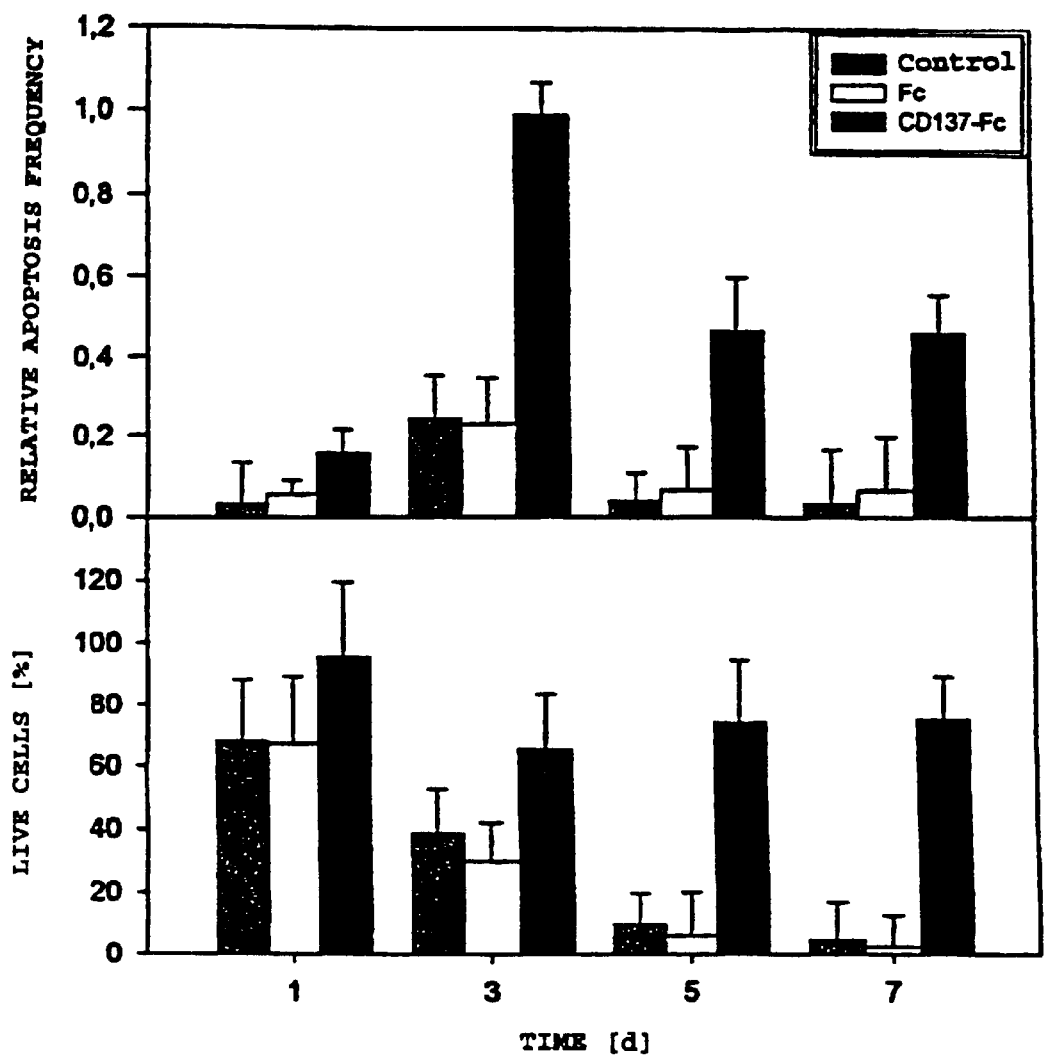
FIG. 2 shows the induction of monocyte apoptosis by CD137.

Isolation, sequencing and characterization of human CD137 were first described by Schwarz, H., et al., in Gene (1993), 134, 295, to which reference is hereby expressly made.

The invention relates, as mentioned, to the use of CD137 and of "functional analogues" thereof. Functional analogues within the meaning of the present invention are in particular variants, derivatives, soluble forms and multimeric forms of CD137 which despite differing from the native form of CD137 have the desired biological activity according to the invention and can thus be employed for the purposes mentioned. In particular, the functional analogues according to the invention must furthermore have the ability to bind to the target cells, i.e. to the peripheral monocytes, in order to be able to induce monocyte proliferation in this way.

CD137 variants include, for example, proteins which are obtainable by one or more amino acid substitutions, deletions, additions, insertions and/or inversions, starting from the sequence shown in FIG. 1A.

Variants of CD137 according to the invention should have an approximately 60 to 100%, such as, for example, approximately 80 to 100%, agreement with the amino acid sequence as shown in FIG. 1A (SEQ ID NO: 2). The modifications of the native amino acid sequence can be produced in a manner known per se, such as, for example, by mutation of the corresponding nucleotides in the nucleotide sequence. Thus the following can be substituted, for example, by one another: amino acids by a similar aliphatic radical, such as isoleucine, valine, leucine and alanine; radicals by a similar polar side group, such as lysine and arginine; such as glutamine and asparagine, or glutamic acid and aspartic acid.

Functional analogues moreover include non-glycosylated or differently glycosylated forms of CD137. The glycosylation pattern can be influenced, for example, by specific choice of the expression system on recombinant preparation of CD137. Moreover, the possibility exists of specifically modifying the amino acid sequence in the region of potential N-glycosylation sites such that glycosylation no longer takes place.

Functional analogues moreover include naturally occurring variants of CD137, which can be obtained, for example, by alternative mRNA splicing or by proteolytic cleavage of CD137 and at the same time can have N- or C-terminal-truncated amino acid sequences. Moreover, variants can be obtained by specifically deleting those terminal or internal amino acids or amino acid subsequences which are not of importance for the desired biological function. For example, cysteine radicals can also be specifically deleted or substituted in order to avoid the formation of incorrect intermolecular disulphide bridges.

Derivatives of CD137 can contain one or more chemical radicals which are bonded via functional side groups of amino acid radicals by chemical or enzymatic modification. Derivatives of CD137 are obtained by derivatization of functional groups of amino acid side chains or on the N-terminus or C-terminus of the protein. For example, glycosyl groups, acyl groups, lipid radicals, phosphate groups, polymer radicals, such as, for example, polyethylene glycol side chains, can be introduced in a manner known per se.

A particular form of derivatization is N- or C-terminal linkage with another amino acid sequence. Fusion proteins of this type can be prepared both chemically and in recombinant manner.

Analogues according to the invention moreover include soluble forms of CD137. These include the extracellular domain of the protein in complete or partial form, while the transmembrane domain is partially or completely deleted. Moreover, these forms do not have the cytoplasmic, C-terminal sequence moiety. According to the invention, soluble forms of CD137 are particularly advantageous in-vivo applications, since as a result, for example, the intravenous administration of a pharmaceutical preparation is markedly simplified. A preferred soluble form of CD137 is a polypeptide with the amino acid residues +18 to +186 as shown in FIG. 1A (SEQ ID NO: 2). Other analogues in the form of soluble or insoluble functional fragments, i.e. partial sequences or combined partial sequences of the native CD137 form, are also included according to the invention.

The soluble forms of CD137 according to the invention can be prepared in a manner known per se. For example, a recombinant preparation starting from the appropriately truncated DNA fragment is possible. Moreover, the possibility exists of preparing truncated CD137 forms by specific protease digestion.

Functional analogues to the polypeptide explicitly described in FIG. 1A (SEQ ID NOS: 1 and 2) which can be used according to the invention moreover include functional equivalent polypeptides, such as can be isolated from other mammals or other cellular systems of the same mammal. A functional equivalent in this sense is, for example, the factor isolated from mice and described in U.S. Pat. No. 5,674,704, having the name 4-1BB, and the functional analogues in turn derived therefrom, such as, for example, fragments.

CD137 and its functional analogues described above can be employed according to the invention both in monomeric form and in multimeric form.

For use in monomeric form, immobilization of the protein is particularly expedient. Immobilization can in this case be carried out on a carrier matrix in a manner known per se. This carrier matrix can be, for example, the surface of a culture vessel in which a monocyte-containing cell system can be cultured. A further suitable carrier matrix can be, for example, polymer particles which are suspensible in a monocyte-containing culture system.

The optimum number of immobilized molecules per unit area can be easily determined by the person skilled in the art by means of a few preliminary experiments. It can be, for example, approximately $10^{11}$ to $10^{17}$ CD137 molecules or of the functional analogues thereof per square centimetre, in particular approximately $10^{13}$ to $10^{14}$, such as, for example, approximately $6\times10^{13}$.

The immobilization can be carried out in any customary manner known to the person skilled in the art, as long as the desired biological activity of the immobilized CD137 molecule is not adversely affected or only insignificantly adversely affected as a result. Immobilization can be carried out, for example, by adsorption of the molecule on a carrier or by covalent linkage to the carrier, e.g. using difunctional linker molecules which are bonded, for example, via functional groups of amino acid residues. In this case, for example, amide, diazo, isothiocyanate or disulphide bridges can be formed between the linker and CD137 (cf., for example, Vitetta et al., 1987, Science 238, 1098; Pastan, et al., 1986, Cell, 47, 641; or Thorpe et al., 1987, Cancer Res. 47, 5924).

A further possibility of immobilization consists in the expression of CD137 on the cell surface of cells transformed with CD137-coding DNA, such as, for example, CHO cells.

The possibility further exists of specifically modifying the CD137 amino acid sequence in order to facilitate immobilization. Modifications of this type are, for example, so-called "tags" functioning as anchors, such as, for example, the modification known as a hexa-histidine anchor, or epitopes which can be recognized as antigens by antibodies (described, for example, in Harlow, E. and Lane, D., 1988, Antibodies: A Laboratory Manual, Cold Spring Harbor (N.Y.) Press). These anchors can serve for the attachment of CD137 to a solid support, such as, for example, a polymer matrix which, for example, can be present in a chromatography column, a microtitre plate or a culture vessel.

A particularly suitable embodiment of a functional analogue of CD137 suitable for immobilization is a fusion protein from the extracellular domain of CD137 and the Fc part of an IgG molecule. Fusion molecules of this type can be particularly advantageously immobilized on supports to which either protein A or an anti-Fc antibody is bound. The preparation of CD137-Fc is described in Schwarz, H. et al., Blood, 87, 7 (1996), 2839–2845, to which reference is hereby expressly made.

Multimeric aggregates of CD137 which can be used according to the invention preferably comprise 2 to 5 CD137 molecules or functional analogues thereof. The aggregation of the individual peptide molecules has to take place such that binding thereof to monocytes is not prevented. Preferably, multimeric CD137 aggregates are prepared from the fusion molecules described above, which include the extracellular domain of CD137 and the Fc part of an IgG molecule. The dimerization can be carried out, for example, by crosslinkage with an anti-Fc antibody. A dimeric aggregate of CD137 is obtained in this way. Dimerization is moreover achievable by formation of disulphide bridges between the Fc part of two fusion protein molecules. Dimerization is also possible by use of bifunctional chemical linkers, such as, for example, those having terminal sulphydryl groups, such as dithiobis(succinimidyl) propionate, N-succinimidyl 3-(2-pyridyldithio)propionate, or reactive carbodiimides, such as, for example, 1-ethyl-3-(3-dimethylaminopropyl)carbodiimide hydrochloride.

Higher multimers, such as, for example, molecules having five CD137 units, are obtainable starting from the Fc part of pentameric IgM molecules and the extracellular domain of CD137.

A first subject of the invention relates to the use of the cell surface protein CD137 designated monocyte growth factor, which is produced by activated T lymphocytes, or a functional analogue thereof for the production of a medicament for promoting the proliferation of peripheral monocytes, if appropriate also of progenitor and/or precursor cells (see below) thereof, of a mammal.

A "promotion" of the monocyte proliferation within the meaning of the invention includes both inducing the proliferation of non-proliferating monocytes and additionally assisting already proliferating monocytes.

Peripheral monocytes are a constituent of the peripheral blood system and in adults are contained in a concentration of 80 to 540 and in children in a concentration of 80 to 720 cells per $\mu$l of blood under physiological conditions.

As is known, different disease states are associated with a decrease in the number of monocytes and/or cells derived therefrom, in particular macrophages of differing tissue specificity (cf. above). On account of the known physiological functions of monocytes and cells derived therefrom, it can moreover be concluded that an increase in the monocyte count, e.g. from a value in the lower physiological range to a higher physiological value, could likewise be of therapeutic benefit as a result of increased proliferation. Moreover, it is conceivable that as a result of artificial induction of monocytosis (increase in the monocyte count in the blood to values of more than 540 cells per $\mu$l of blood), the monocytic defence system of the body is assisted during defence against infections.

A further subject of the present invention therefore relates to the use of CD137 or of a functional analogue thereof for the production of a medicament for treating a condition which is associated with a disorder of a cell system which includes monocytes and/or cells derived therefrom and/or progenitors and/or precursors thereof, in particular monocytes and/or cells derived therefrom, such as macrophages (cf. schematic representation of the haematopoietic system in Concepts of Gene Therapy, (1997) Verlag Walter de Gruyter Berlin, Strauss, M., and Barranger, J. A. (Ed.), p. 236, Table 12.1 to which reference is hereby expressly made); or whose formation and/or course is treatable by promoting the proliferation of cells of this cell system.

A disorder in the above sense can in this case include an inherited or acquired, permanent or temporary, partial or complete impairment of one or more physiological functions of the body cells concerned.

Such a cell system is, for example, the so-called myeloid cell system, whose cells are derived from progenitor cells from the bone marrow. Typical constituents of this system are granulocytes and monocytes.

In particular, the use according to the invention is indicated when the disorder mentioned includes a functional disorder or a decrease in the monocyte count below a concentration of 80 cells per μl of blood, and/or a decrease in cells derived therefrom.

A first preferred field of application for CD137 are conditions according to the invention which are selected from chemotherapy- or radiation therapy-related damage to the haematopoietic system. Chemotherapy and radiation therapy are frequently carried out for the treatment of all sorts of oncoses or, in the context of a myelosuppressant or myeloablative therapy, for the preparation of bone marrow or organ transplants. Leucopenia and a decrease in the monocyte count associated therewith is frequently a result here. Morbidity and mortality of the patients on account of raised susceptibility to infection greatly increase. The leucopenia could be more effectively alleviated or eliminated by administration according to the invention of CD137 or CD137-treated monocytes.

A further field of application relates to the use of CD137 or functional analogues for the treatment of wound healing disorders, such as are to be observed, for example, in dialysis patients or diabetics or patients with chronic venous insufficiency. In this case, these are wound healing disorders which result from insufficiently present or functioning granulation tissue, which mainly consists of macrophages (i.e. differentiated monocytes).

A further subject of the invention relates to the use of CD137 or a functional analogue thereof for the production of a medicament for treating conditions which are associated with an inadequate immune response. Examples of conditions of this type which may be mentioned are:

a) Oncoses which are favoured by inadequate or absent cytotoxic activity of the endogenous defence system.

b) Bacterial, viral and fungal infections which are favoured by an inadequate or absent phagocytosis of the pathogen or body cells infected therewith.

Furthermore, treatment of c) inherited or non-inherited, acquired or non-aquired damage to or conditions of the immune system; and d) damage induced by treatment with immunosuppressants, such as can occur, for example, in the treatment of patients with chronic polyarthritis or autoimmune disorders or of transplant patients.

As will be explained even more precisely in a later section, the medicament according to the invention can be employed in the context of an in-vivo or ex-vivo treatment.

According to a further embodiment of the invention, CD137 or a functional analogue thereof can also be used in combination with at least one further factor which is selected from interleukins, lymphokines, monokines, interferons, colony-stimulating factors and growth factors. Non-limiting examples which may be mentioned are: IL-1, IL-2, IL-3, IL-4, IL-5, IL-6, IL-7, IL-8, IL-9, IL-10, IL-11, IL-12, IFN-α, -β, -γ, TNF-α, EGF, TGF, PDGF, ILGF, MGF, EPO, G-CSF, GM-CSF and M-CSF, leucocyte-stimulating factors, such as G-CSF, GM-CSF and especially M-CSF being preferred. CD137 and the further factor can be administered here simultaneously or sequentially in any desired sequence.

Combined use with apoptosis-inhibiting factors is conceivable. Possibly, M-CSF has an inhibiting effect of this type on monocyte apoptosis.

For use in the context of the present invention, human CD137 is fundamentally suitable in its native form, i.e. as a protein having an amino acid sequence of residue +18 to residue +255 in the sequence according to FIG. 1A (SEQ ID NO: 2) or a functional analogue of this sequence.

Preferably, however, the extracellular domain of human CD137 corresponding to the amino acids +18 to +186 as shown in FIG. 1A (SEQ ID NO: 2) or a functional analogue thereof is used.

In a preferred embodiment of the invention, CD137 or its functional analogue is employed in immobilized form or as a multimeric aggregate.

A preferred multimeric CD137 aggregate comprises 2 to 5 CD137 protein molecules or functional analogues thereof.

The invention moreover relates to an in-vitro or ex-vivo process for promoting the proliferation of peripheral monocytes, peripheral monocytes from the blood of a mammal being brought into contact with free or immobilized, in particular immobilized, CD137 in a nutrient medium and incubated until the monocyte count has increased, preferably to its maximum value, and/or an increase in the monocytes can be observed.

The isolation of monocytes from the blood of a mammal can be carried out according to generally customary standard methods. The isolated cell fraction can be either a pure monocyte fraction or can contain cells which do not adversely affect the treatment of the monocytes and the subsequent treatment of the mammal with the stimulating monocytes. Thus lymphocytes, for example, can be present during the in-vitro incubation phase in addition to the monocytes. Suitable methods for the isolation of monocytes are described, for example, in Meyskens, F. L., et al, Exp. Haematol. 1979, 7(8), 401–410; Weiner, R. S., et al., J. Immunol. Methods, 1980, 36(2), 89–97; and Contreras, T. J., et al., Cell. Immunol., 1980, 54(1), 215–229.

A non-limiting example of a nutrient medium suitable for in-vivo or ex-vivo culturing is, for example, RPMI medium supplemented with 5% foetal calf serum. After completion of the culturing, it is expedient to wash the treated monocyte fraction, such as, for example, with PBS, before it is administered again to the mammal to be treated.

A further subject of the invention relates to the use of CD137 or of a functional analogue in a process for the regenerative treatment of chemotherapy or radiation therapy patients, where a) a blood fraction containing peripheral monocytes is isolated from the blood of the patient before carrying out the chemotherapy or radiation therapy, this is incubated ex vivo with free or immobilized, in particular immobilized, CD137 until the monocyte count increases, or has reached its optimum, and/or an increase in size of the monocyte is to be observed, and the blood fraction treated in this manner and preferably enriched with monocytes is administered to the patient again after completion of the therapy; or b) an efficacious amount of a multimeric CD137 aggregate is administered to the patient before, during or after completion of the chemotherapy or radiation therapy to promote the proliferation of the endogenous peripheral monocytes.

A further subject of the invention relates to the use of CD137 or of a functional analogue in a process for promoting the endogenous non-specific immune defence, where an amount of CD137 or a functional analogue thereof promoting the proliferation of peripheral monocytes, in particular an amount of a multimeric CD137 aggregate promoting the proliferation of peripheral monocytes, is administered to a patient. This process is particularly suitable for carrying out on tumour patients and patients who are suffering from a bacterial, viral or fungal infection.

A multimeric CD137 aggregate which is advantageously administrable in the context of this process comprises 2 to 5 CD137 protein molecules or functional analogues thereof.

The administration of such analogues or aggregates which comprise the extracellular section of human CD137 corresponding to the amino acids +18 to +186 as shown in FIG. 1A (SEQ ID NO: 2) or of a functional analogue thereof capable of binding to monocytes is particularly suitable.

For in-vivo administration, it is advantageous to use human CD137 or an analogue derived therefrom. If CD137 is administered as a fusion protein, the protein fused to CD137 should likewise be of human origin. Further measures for improving the residence time of CD137 in the blood, such as, for example, by PEGylation, such as has already been successfully used, for example, for other cytokines (cf. PEGylation of G-CSF, described in EP-A-0 335 423), are also conceivable.

The particular choice of the dosage of CD137 or of a functional analogue thereof and the particular dosage schedule are incumbent on the decision of the treating physician. The latter, depending on the selected administration route, on the efficacy of the particular medicament, on the nature and severity of the condition to be treated, on the condition of the patient and his/her response to the therapy, will select a suitable dose and a corresponding dosage schedule. However, a suitable dose should generally be in the range from approximately 1 to 20 µg/kg of body weight/day or in the range from approximately 0.01 to 1 nmol/kg of body weight/day.

Based on blood volume, efficacious concentrations of CD137 or of a functional analogue thereof during the therapy can be in the range from approximately 0.01 µg to 10 µg per millilitre of blood or in the range from approximately 0.1 pmol to 0.5 nmol per millilitre of blood.

For in-vitro or ex-vivo administration, efficacious concentrations of CD137 or of a functional analogue thereof can be in the range from not more than approximately 0.1 µg/ml of medium, in particular more than approximately 1 µg/ml of medium, such as, for example, up to approximately 50 µg/ml of medium, or in the range from more than approximately 1 pmol/ml of medium, in particular more than approximately 0.01 nmol/ml of medium, such as, for example, approximately 2 nmol/ml of medium.

The in-vivo administration of CD137 and the functional analogues thereof is advantageously carried out using a parenterally, in particular intravenously, administrable, liquid pharmaceutical composition. This preferably contains an efficacious amount of CD137 or a functional analogue thereof, preferably in dissolved form, in a pharmaceutically acceptable vehicle which is suitable for this purpose. Examples of suitable pharmaceutical vehicles are, in particular, aqueous solutions, such as, for example, physiological saline solution, phosphate-buffered saline solution, Ringer's solution, lactated Ringer's solution and the like.

Moreover, the composition can contain further additives, such as antioxidants, chelating agents, or antimicrobial agents. Oral administration and administration by inhalation are also possible.

Intravenous administration is particularly expedient if systemic therapy is necessary. For the treatment of local conditions, such as, for example, locally restricted infections, specific subcutaneous or intradermal administration can also be advantageous. For local wound treatment, for example, superficial, cutaneous administration is possible. This can be carried out by application of a solution, of a suspension, of an ointment or of a gel.

The optimum concentration of CD137 or of a functional analogue thereof in the pharmaceutical compositions according to the invention is determined, inter alia, by the specific activity of the form of CD137 used. Suitable proportions by weight of CD137 or of a functional analogue thereof should, however, be in the range from approximately 0.0001 to 1% by weight, in particular 0.0005 to 0.01% by weight, based on the total weight of the composition. The molar concentration, for example, can be in the range from approximately 1 nmol to 0.1 mmol, in particular approximately 15 to 300 nmol per 100 g of the composition employed.

The invention moreover relates to the use of a nucleotide sequence which codes for CD137 or a functional analogue thereof for the production of a gene therapy composition for the treatment of one of the conditions defined above.

Figure 12:
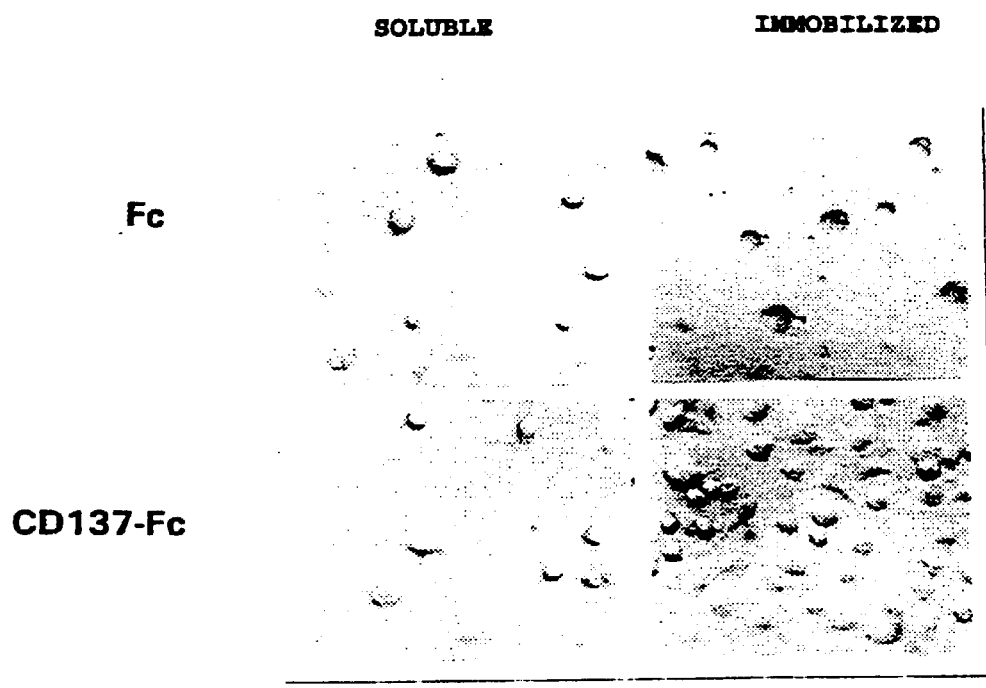
FIG. 12 shows monocytes after 8 day's culturing at 300 times magnification in the presence of soluble or immobilized Fc or CD137-Fc protein (in each case 1 µg/ml).

Gene therapy compositions of this type comprise a cellular vehicle, in particular peripheral monocytes, cells derived therefrom or progenitor cells or precursors of the monocytes (cf. schematic representation of the haematopoietic system in Concepts of Gene Therapy, (1997) Verlag Walter de Gruyter Berlin, Strauss, M., and Barranger, J. A. (Ed.), p. 236, FIG. 12.1; to which reference is hereby expressly made), in which the coding nucleotide sequence for CD137 or for a functional analogue thereof is incorporated in expressible form in a suitable nucleic acid construct.

The invention furthermore relates to a gene therapy process for the treatment of one of the conditions defined above, in which a gene therapy composition according to the invention is administered to the patient.

To this end, the gene transfer to the cells mentioned can be carried out in a manner known per se, such as, for example, with the aid of viral constructs, non-viral vehicles, such as liposomes or other suitable nucleic acid constructs (Günzburg, W. H. et al., Gentransfer in Säugerzellen, [Gene Transfer in Mammalian Cells], (1997) Spektrum Akademischer Verlag, Heidelberg, Berlin; Baum, C., et al., Gene Transfer and Transgene Expression in Haematopoietic Cells, in Concepts of Gene Therapy, (1997), Verlag Walter de Gruyter Berlin, Strauss, M., and Barranger, J. A. (Ed.) pp. 233–256).

The nucleic acid construct which can be used according to the invention is combined, for example, with a virus vector such as, for example, with an adenovirus vector or a replication-deficient adenovirus vector, or ligated with an adeno-associated virus vector.

A further advantageous combination is the complexation of the nucleic acid constructs with liposomes. During lipofection, small unilamellar vesicles are prepared from cationic lipids by ultrasonic treatment of the liposome suspension. The DNA is bound ionically to the surface of the liposomes, to be precise in such a ratio that a positive net charge remains and the DNA is complexed to 100% of the liposomes. In addition to the lipid mixtures of DOTMA (1,2-dioleyloxypropy-3-tri-methylammonium bromide) and DOPE (dioleoylphosphatidy-ethanolamine), in the meantime numerous novel lipid formulations have been synthesized and tested for their efficiency of transfection of various cell lines (Behr, J. P. et al., (1989) Proc. Natl. Acad. Sci USA 86, 6982–6986; Felgner, J. H. et al., (1994) J. Biol. Chem. 269, 2550–2561; Gao, X. & Huang, L. (1991) Biochem. Biophys. Res. Commun. 179, 280–285; Zhou, X. & Huang, L. (1994) Biochem. Biophys. Acta 1189, 195–203). Examples of the novel lipid formulations are DOTAP N-[1-(2,3-dioleoyl-oxy)propyl]-N,N,N-trimethylammonium methylsulphate or DOGS (TRANSFECTAM; dioctadecylamidoglycylspermine).

In addition to the nucleotide sequence coding for CD137 or a functional analogue thereof, nucleic acid constructs which can be used according to the invention include in functional, operative linkage one or more regulatory sequences, such as promoters, amplification signals, enhancers, polyadenylation sequences, replication origins, reporter genes, selectable marker genes and the like. Depending on the desired application, this linkage can lead to an increase or decrease in gene expression.

Additionally to the newly introduced regulation sequences, the natural regulation sequence can still be present before the actual structural genes. By means of genetic modification, this natural regulation can optionally be switched off and the expression of the genes increased. The gene construct, however, can also be of simpler construction, that is to say no additional regulation signals are inserted before the structural genes and the natural promoter with its regulation is not removed. Instead of this, the natural regulation sequence is mutated such that regulation no longer takes place and gene expression is increased. Additional advantageous regulatory elements can also be inserted at the 3' end of the nucleic acid sequences. The nucleic acid sequences can be present in one or more copies in the gene construct.

In principle, all natural promoters with their regulation sequences can be used. Moreover, even synthetic promoters can advantageously be used. The regulatory sequences should preferably make possible the specific expression of the nucleic acid sequences.

A further variant of treatment forms according to the invention relates to the use of CD137-specific antibodies or other CD137 antagonists which inhibit or decrease the proliferation-promoting action of CD137, whereby the CD137 therapy could optionally be further optimizable.

The invention therefore also relates to the antibodies or fragments thereof which can be used for this purpose, which are accessible in a manner known per se, and correspondingly suitable other CD137 antagonists. Conditions which are accompanied by increased formation of monocytes, such as, for example, certain forms of blood cancer, would optionally be treatable with CD137 antagonists of this type.

The present invention is now explained in greater detail with the aid of the following non-limiting working examples.

WORKING EXAMPLES

Reagents

M-CSF and neutralizing antibodies against M-CSF, GM-CSF and IL3 were obtained from R&D (Wiesbaden, Germany). Anti-M-CSF: clone 26730,11, protein A-purified IgG fraction from the ascites fluid of mouse hybridoma. Anti-GM-CSF: clone 3209.1, monoclonal $IgG_1$ mouse antibody; anti-IL3: protein A-purified IgG fraction from the ascites fluid of mouse hybridoma. Recombinant CD137-Fc protein, consisting of the extracellular domain of human CD137 and the constant domain of human immunoglobulin $G_1$ (Fc) was obtained from Alexis (Grünberg, Germany).

Human $IgG_1$ Fc protein was obtained from the Accurate Chemical and Scientific Corporation (Westbury, N.Y., USA).

Reference Example 1

Immobilization of CD137-Fc

Polystyrene microtitre plates (Microtest III Tissue Culture Plates; Becton Dickinson, Franklin Lakes N.J., USA) were incubated overnight at 4° C. with a solution of 1 µg/ml of CD137-Fc protein in PBS (phosphate-buffered saline solution). 50 µl of the solution were used per well. The next morning, the protein solution was removed and the plates were washed with PBS. The immobilization of Fc was carried out analogously.

Reference Example 2

Elisa

ELISA kits were obtained from R&D Systems (Wiesbaden, Germany). The test was carried out according to the instructions of the manufacturer. Cytokine concentrations were determined in triplicate using the test and expressed as the average value±standard deviation.

Reference Example 3

Determination of the Apoptosis of Monocytes

DNA fragmentation was determined with the aid of the "Cell Death Detection ELISA" (Boehringer Mannheim, Germany) according to the instructions of the manufacturer. The measurements were carried out in triplicate.

Reference Example 4

Isolation and Culturing of Human Monocytes

Human peripheral blood mononuclear cells (PBMC) were isolated from buffy coats of healthy subjects. For this, buffy coats were diluted with two equal volumes of BS. An equal volume of Histopaque (Sigma, Deisenhofen, Germany) was covered with a layer. This mixture was centrifuged at 1200 g for 20 min. PBMCS, which enriched on the Percoll separating surface in the form of a white layer, were isolated. Erythrocytes were lysed at room temperature for 2 min using 2 ml of 200 mM $NH_4Cl$, 10 mM $NaHCO_3$, 10 mM EDTA, pH 7.4. The cells were washed twice with PBS, pelleted at 250 g and resuspended in RPMI medium, supplemented with 5% foetal calf serum.

The primary monocytes were isolated therefrom by elutriation (Andreesen, R., et al., J Leukoc Biol 47:490, 1990). The elutriated monocytes were pure to 95% and the content of T lymphocytes was less than 3% (estimated by means of the morphology and of the antigen phenotype, i.e. expression of DC14, DC3, CD4 and CD8). The cells were cultured in polystyrene culture dishes (Becton Dickinson, Franklin Lakes, N.J., USA) in RPMI 1640 medium, supplemented with 5% FCS, at the cell concentration indicated in each case.

Reference Example 5

Determination of the Cell Proliferation

For measurement of the proliferation of individual cells, the "In Situ Proliferation Kit" from Boehringer Mannheim, Germany, was used. 3×10⁵ cells were inoculated per chamber of an 8-chamber carrier (FALCON, Becton Dickinson, Heidelberg, Germany), which had been coated with Fc or CD137-Fc protein, and cultured for 10 days. 10 $\mu$M bromodeoxyuridine (BrdU) was added over 60 min. Incorporated BrdU was visualized according to the test instructions by staining with mouse anti-BrdU and sheep anti-mouse FITC. Monocytes were identified by staining with phycoerythrin-labelled anti-CD14 antibody (2 $\mu$g/ml; Immunotech, Marseille, France). Chromatin was stained for 5 min with 5 $\mu$g/ml of Hoechst 33342 (Sigma, Deisenhofen, Germany).

The proliferation of cell populations was determined in a 96-hole microtitre plate. 10⁵ monocytes per hole were pulsed with 0.5 $\mu$Ci ³H-thymidine for 24 h, harvested and measured using a TopCount microplate scintillation counter (Packard, Meriden, Conn., USA). Each batch was counted three times and the results are indicated as the average values±standard deviations.

Example 1

CD137-Fc Induces Apoptosis in Monocytes

10⁵ primary monocytes were cultured on tissue culture dishes which had previously been coated with a fusion protein which consisted of the extracellular domain of CD137 and the constant domain of human immunoglobulin $G_1$ (Fc). Untreated plates and plates coated with Fc protein were used as controls. In the wells coated with CD137-Fc protein, the number of live monocytes on days 1, 3, 5 and 7 of culturing was significantly increased (FIG. 2, lower half). The degree of apoptosis in the same cultures was determined by means of the amount of fragmented DNA (FIG. 2, upper half). Surprisingly, a higher degree of apoptosis was found in monocyte cultures which had been treated with CD137-Fc protein. Comparable results were obtained in three independent experiments.

Example 2

Figure 3A:
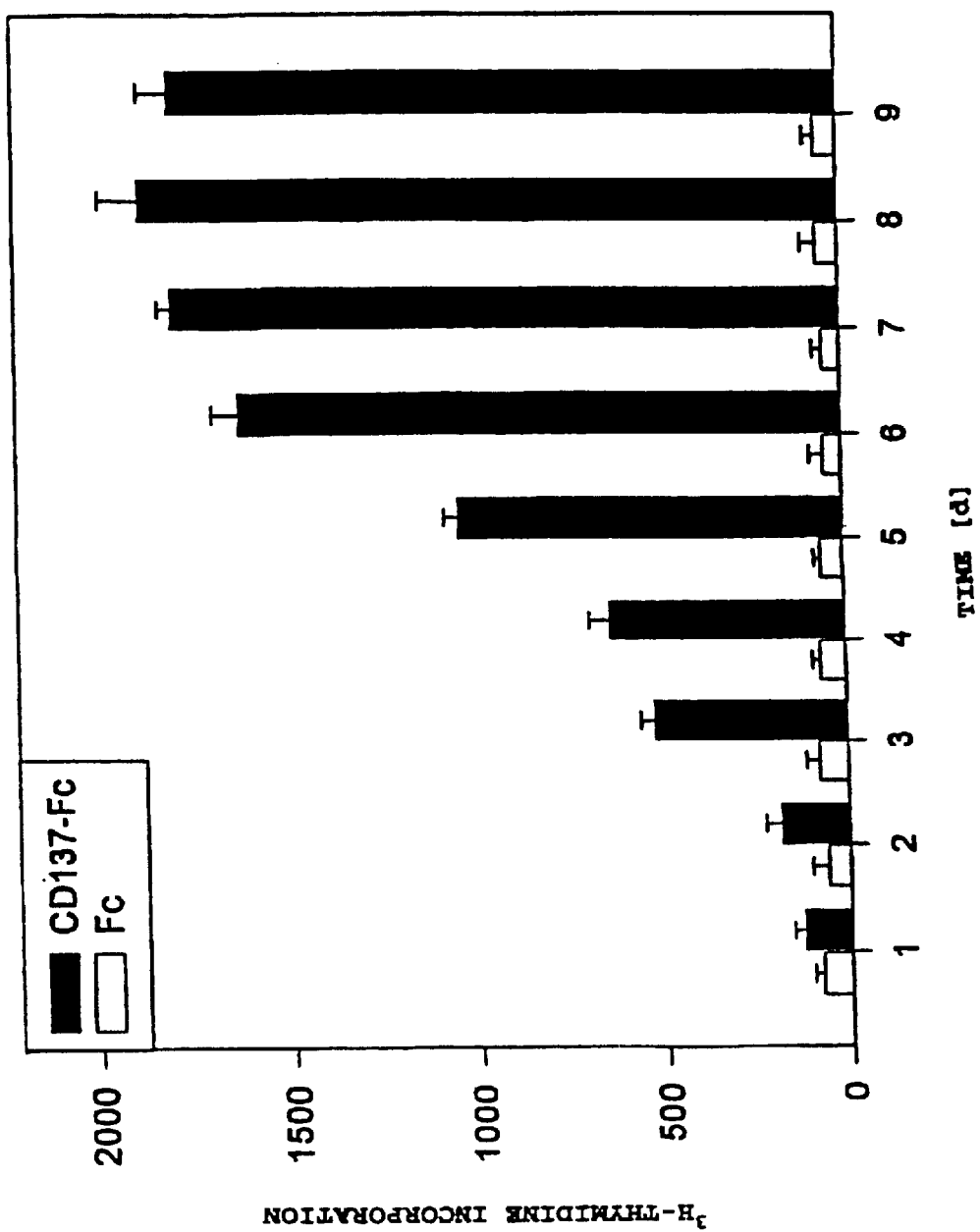
FIG. 3 (A) shows the induction of the proliferation of peripheral monocytes by immobilized CD137-Fc protein with the aid of $^3$H-thymidine incorporation; (B) the CD137-induced colony formation of monocytes.

CD137-Fc Induces the Proliferation of Peripheral Monocytes and Brings About Colony Formation of the Monocytes (a) CD137 induced a strong proliferation of monocytes, which overcompensated the loss of cells by likewise-induced apoptosis. 10⁵ monocytes were cultured in 96-hole plates coated with Fc or CD137-Fc. The proliferation was determined daily by a 24-hour pulse with 0.5 $\mu$Ci of ³H-thymidine. As the ³H-thymidine incorporation rates showed, CD137-Fc in fact induced a strong monocyte proliferation (FIG. 3A). The proliferation showed a positive correlation with the culturing time of the monocytes in the presence of CD137-Fc protein. The induction of the proliferation reached a maximum after 7 to 10 days, the ³H-thymidine incorporation being increased 30-fold or more in comparison with control cells. No difference was found between the monocytes in untreated wells and those coated with Fc protein (results not shown).

The substantial increase in ³H-thymidine uptake is in agreement with the finding that the CD137-Fc-induced proliferation took place in the culture in a widely distributed manner. On labelling of the CD137-treated monocytes by means of a one-hour treatment with bromodeoxyuridine (BrdU) and subsequent detection with a fluorescein-labelled anti-BrdU antibody, it was, specifically, found that 9.3% of the cells (55±6 of 589±43) replicated their DNA, while peripheral monocytes which were grown on Fc coated carriers showed no incorporation of BrdU (results not shown).

By means of immunocytochemical investigations, it was moreover possible to confirm that the proliferating cells were in fact monocytes and not other blood cells. Specifically, the proliferation was determined, as described above, by BrdU incorporation and the identity of the monocytes was verified by simultaneous staining of CD14, a cell-surface protein specific for monocytes. The nuclei were rendered visible by staining with the DNA intercalation dye Hoechst 33342. In these investigations, it was found that the proliferating cells had typical features of monocytes: they were CD14-positive, polynuclear and showed the typical morphology of monocytes/macrophages (results not shown).

Figure 3B:
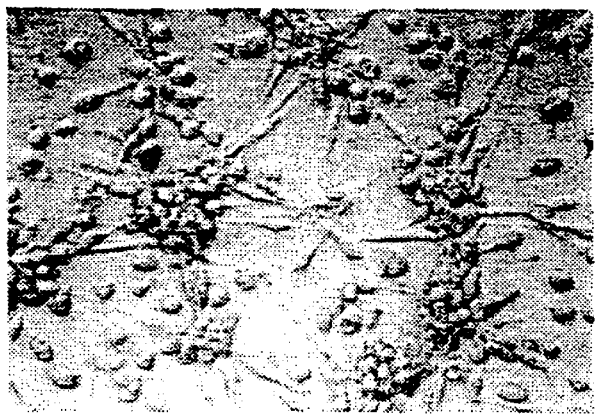

(b) As the micrograph according to FIG. 3B shows, treatment according to the invention of monocytes with immobilized CD137-Fc leads to significant colony formation, as has also already been shown for other haematopoietic growth factors.

Example 3

M-CSF and GM-CSF are Essential Additional Factors for CD137-induced Monocyte Proliferation (a) 10⁵ peripheral monocytes were cultured over immobilized Fc or immobilized CD137-Fc. Neutralizing anti-M-CSF antibodies (2 $\mu$g/ml), anti-GM-CSF antibodies (2 $\mu$g/ml) and anti-IL-3-antibodies (2 $\mu$g/ml) were added according to the experimental plan. The proliferation was determined on day 10 by means of ³H-thymidine incorporation.

It was possible to achieve complete inhibition of monocyte proliferation by means of neutralizing anti-M-CSF and anti-GM-CSF antibodies. Neutralizing anti-GM-CSF antibody on its own only brought about an 18% decrease in proliferation. Anti-IL-3 antibody had no effect on the CD137-induced proliferation. The addition of anti-GM-CSF and anti-IL-3 antibodies led to a synergistic decrease in the proliferation to a third of the original value (cf. FIG. 4A).

These results illustrate that M-CSF and GM-CSF were significant factors for the CD137-induced proliferation of peripheral monocytes.

Figure 4B:
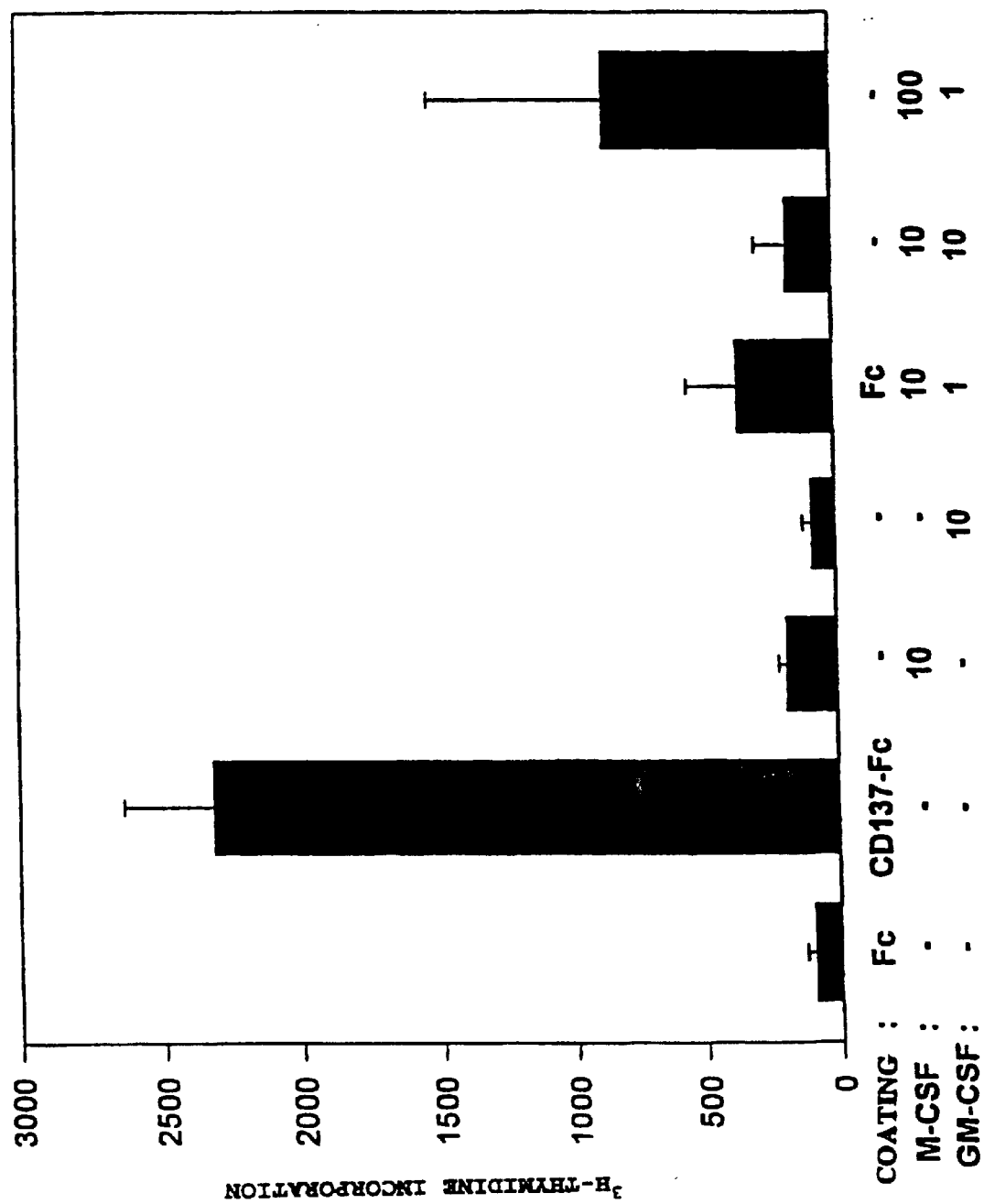
FIG. 4 shows the effects of M-CSF and GM-CSF on the CD137-induced monocyte proliferation; (A) Culturing of peripheral monocytes on immobilized Fc or CD137-Fc protein in the absence or presence of neutralizing antibodies against M-CSF, GM-CSF and/or IL-3; (B) a proliferation of monocytes is not induced by M-CSF and GM-CSF; in each case the $^3$H-thymidine uptake is shown.

(b) In a further experiment, however, it was found that M-CSF and GM-CSF only caused negligible proliferation at concentrations such as are induced by CD137. Peripheral monocytes were cultured on 96-hole plates, coated with Fc or CD137-Fc protein (1 $\mu$g/ml) or with M-CSF and GM-CSF at the concentrations indicated (ng/ml). The proliferation was determined on day 10 by means of the ³H-thymidine incorporation (FIG. 4B). In preliminary experiments, it was found that M-CSF was induced by CD137 in concentrations of up to 10 ng/ml. It was not possible to measure a GM-CSF induction (results not shown). In vivo, M-CSF and GM-CSF are detectable in concentrations of 10 ng/ml or 50 pg/ml (Kawano, Y., Eur J Haematol 54:147, 1995; Elner, S. G., Curr Eye Res 14:1045, 1995; Saunders, M. A., Br J Pharmacol 120:545, 1997). In the test series shown in FIG. 4B, M-CSF and GM-CSF were employed in significantly higher concentrations in comparison with the literature values, namely 100 and 1 ng/ml respectively. In comparison with CD137, however, it was only possible to induce a fraction of the proliferation due to M-CSF and/or GM-CSF. This can be taken as an indication that additional factors which are induced by means of the action of CD137 in monocytes contributes in an autocrine manner to the CD137-induced monocyte proliferation.

Example 4

Figure 5A:
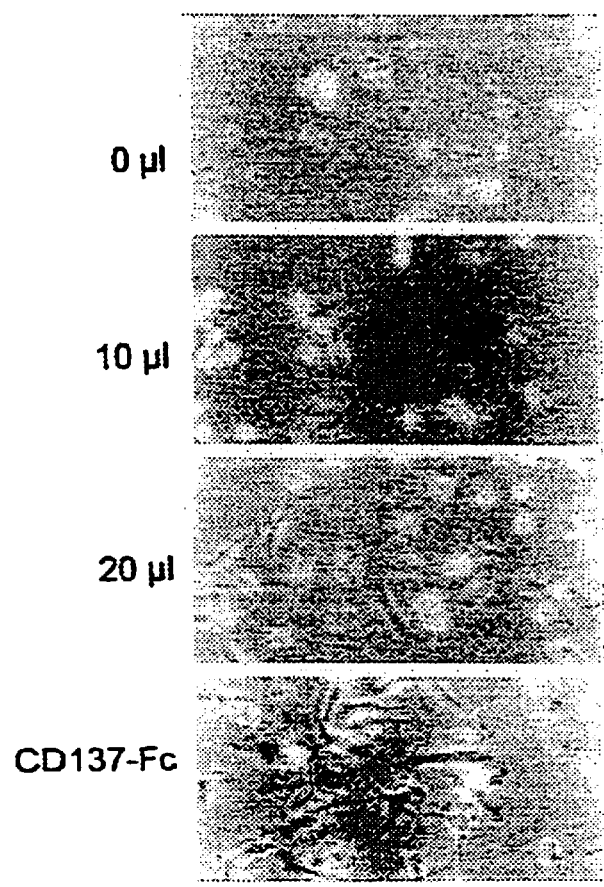
FIG. 5 shows the induction of (A) growth and (B) proliferation of monocytes by conditioned supernatant of cell cultures which have been cultured with CD137-Fc protein.
Figure 5B:
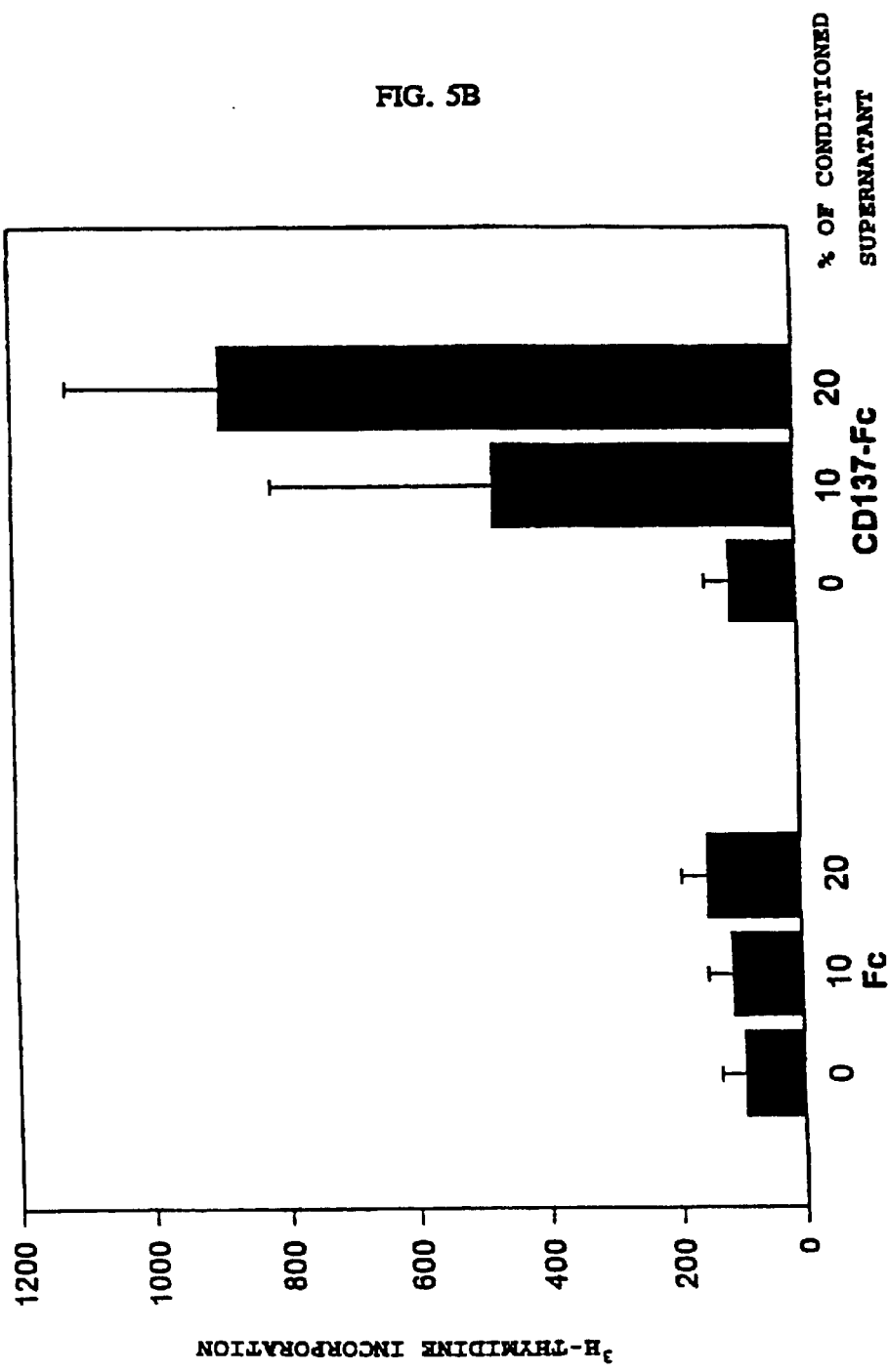

CD137-Fc-induced Monocyte Proliferation is Mediated by One or More Soluble Autocrine Factors The next thing investigated was whether these factors, which were possibly additionally involved in the CD137-induced monocyte proliferation, are present in soluble form or bound to the cell surface. For this, $10^5$ peripheral monocytes were cultured on immobilized Fc or immobilized CD137-Fc protein for 24 h. The cells were removed by centrifugation at 12,000 g for 5 minutes. 0, 10 and 20 μl of conditioned supernatant of these cultures were transferred to 100 μl of fresh cultures of untreated monocytes. The transfer of this conditioned medium to untreated monocytes from the same donor induced cell growth (FIG. 5A) and cell proliferation (FIG. 5B) in a dose-dependent manner. To illustrate the effect on cell growth, the cells were photographed at 300 times magnification after 8 days. For comparison, the lower illustration in FIG. 5A shows monocytes which had been cultured for 8 days on immobilized CD137-Fc protein.

For determination of the proliferation (FIG. 5B), Fc or CD137-Fc were immobilized on culture substrates in the manner described above. Monocytes were then cultured with conditioned supernatant in the concentration indicated. As described above, the proliferation was determined via the $^3$H-thymidine incorporation. For this, pulsing was carried out with 0.5 μCi of $^3$H-thymidine for 24 hours on day 8. Repetition of the experiment three times led to comparable results.

Example 5

Immobilization of the CD137 Protein is Necessary for the Induction of Monocyte Proliferation $10^5$ peripheral monocytes were cultured over immobilized Fc and immobilized CD137-Fc and, for comparison therewith, in the presence of Fc and CD137-Fc in dissolved form. Immobilization of CD137 and Fc was prevented in the comparison batches by blocking the culture vessels non-specifically with bovine serum albumin (incubation with 200 μl of BSA, 0.1% strength, for 30 min. at room temperature).

Figure 6:
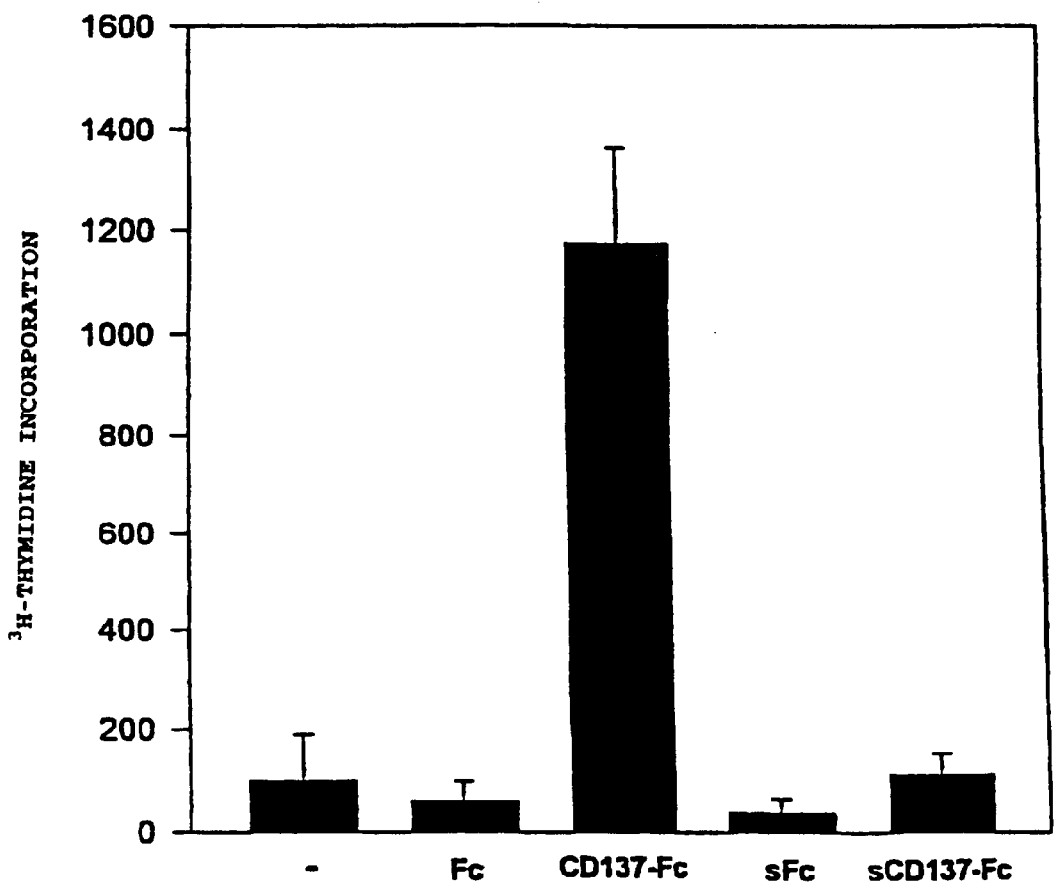
FIG. 6 shows a comparison of the induction of monocyte proliferation by soluble CD137-Fc (sCD137-Fc) and immobilized CD137-Fc; as a control, immobilized Fc, soluble Fc (sFc) and the untreated support are indicated.

The proliferation was determined on day 10 by means of the $^3$H-thymidine incorporation. As the results shown in FIG. 6 show, induction of monocyte proliferation by CD137 could only be observed if CD137 protein was immobilized beforehand by coating tissue culture dishes with the protein. On the other hand, if CD137 was administered as the soluble protein, the induction of proliferation was also markedly decreased. In three independent experiments, three comparable results were obtained.

Example 6

Investigation of Monocyte Proliferation in the Presence of TNFR-Fc and Anti-CD68.

Figure 7:
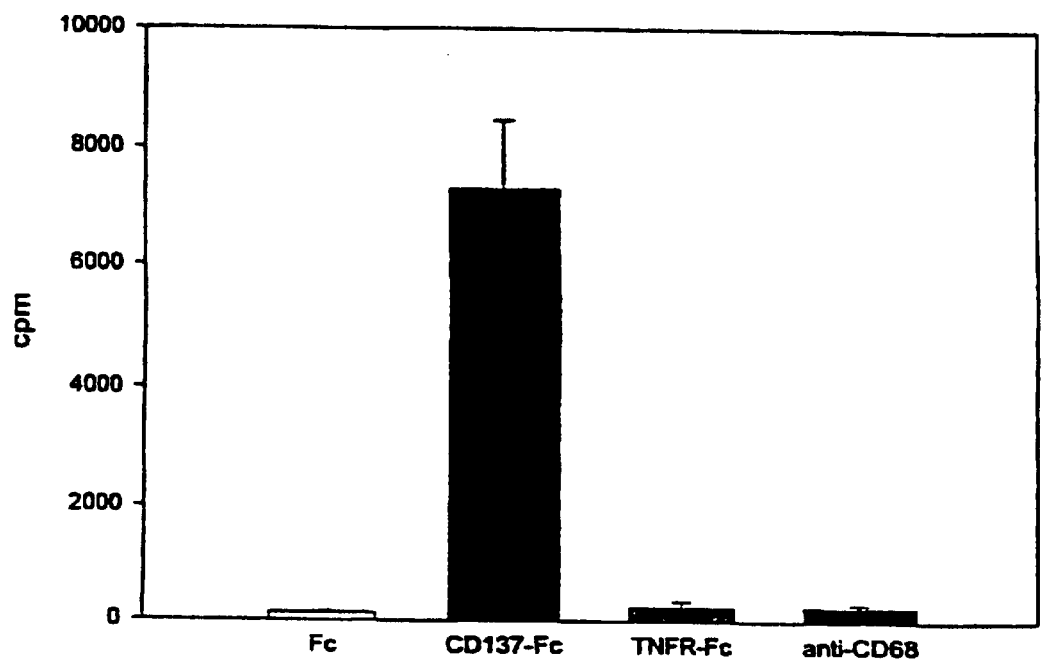
FIG. 7 shows attempts at the induction of monocyte proliferation with Fc, CD137-Fc, TNFR-Fc and anti-CD68.

Fc protein, CD137-Fc protein, tumour necrosis factor receptor (TNFR)-Fc protein and anti-CD68 were immobilized for further characterization of the induction of monocyte proliferation. The $^3$H-thymidine incorporation was determined as described above. It is evident from FIG. 7 that only CD137-Fc induces monocyte proliferation significantly.

TNFR-Fc and anti-CD68 are both proteins which bind to the surface of monocytes similarly to CD137. With their use as a control, it should be excluded that only the binding of monocytes to the surface of the culture vessel causes the observed effects.

Example 7

CD137 and M-CSF Additively Induce Monocyte Proliferation $10^5$ monocytes per well were introduced into a 96-hole microtitre plate. Each well had previously been coated with Fc or CD137-Fc (in each case 1 μg/ml). M-CSF (100 μg/ml) and LPS (lipopolysaccharide) (50 μg/ml) were added in dissolved form. Measurement of the proliferation after culturing for 8 days was carried out by means of the $^3$H-thymidine incorporation after a 24-hour pulse with 0.5 μCi of $^3$H-thymidine.

Figure 8:
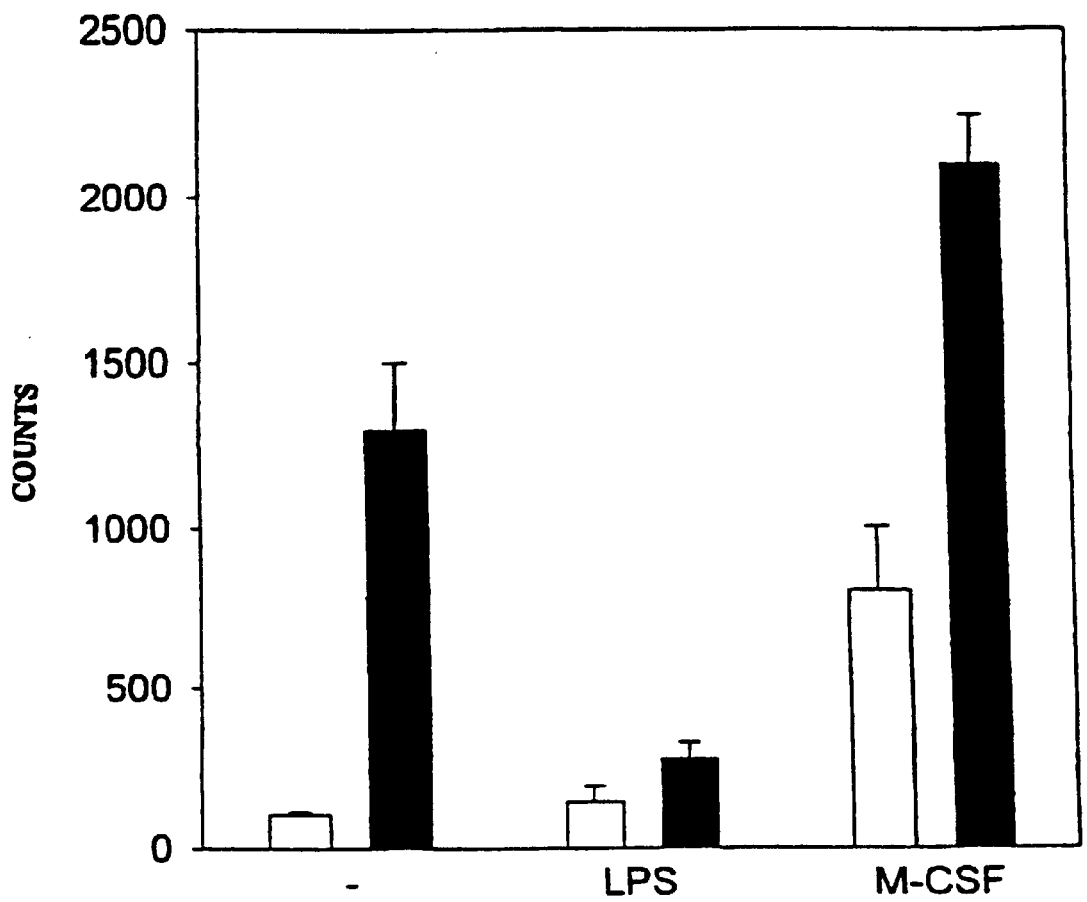
FIG. 8 shows attempts at the induction of monocyte proliferation with Fc (light bars) or CD137-Fc (black bars) combined with LPS or M-CSF.

As the experimental results shown in FIG. 8 show, the $^3$H-thymidine incorporation in monocytes is increased additively by immobilized CD137-Fc or M-CSF. On the other hand, LPS does not lead to any significant increase in the incorporation rate, and thus has no effect on the CD137-induced monocyte proliferation.

Example 8

Figure 9A:
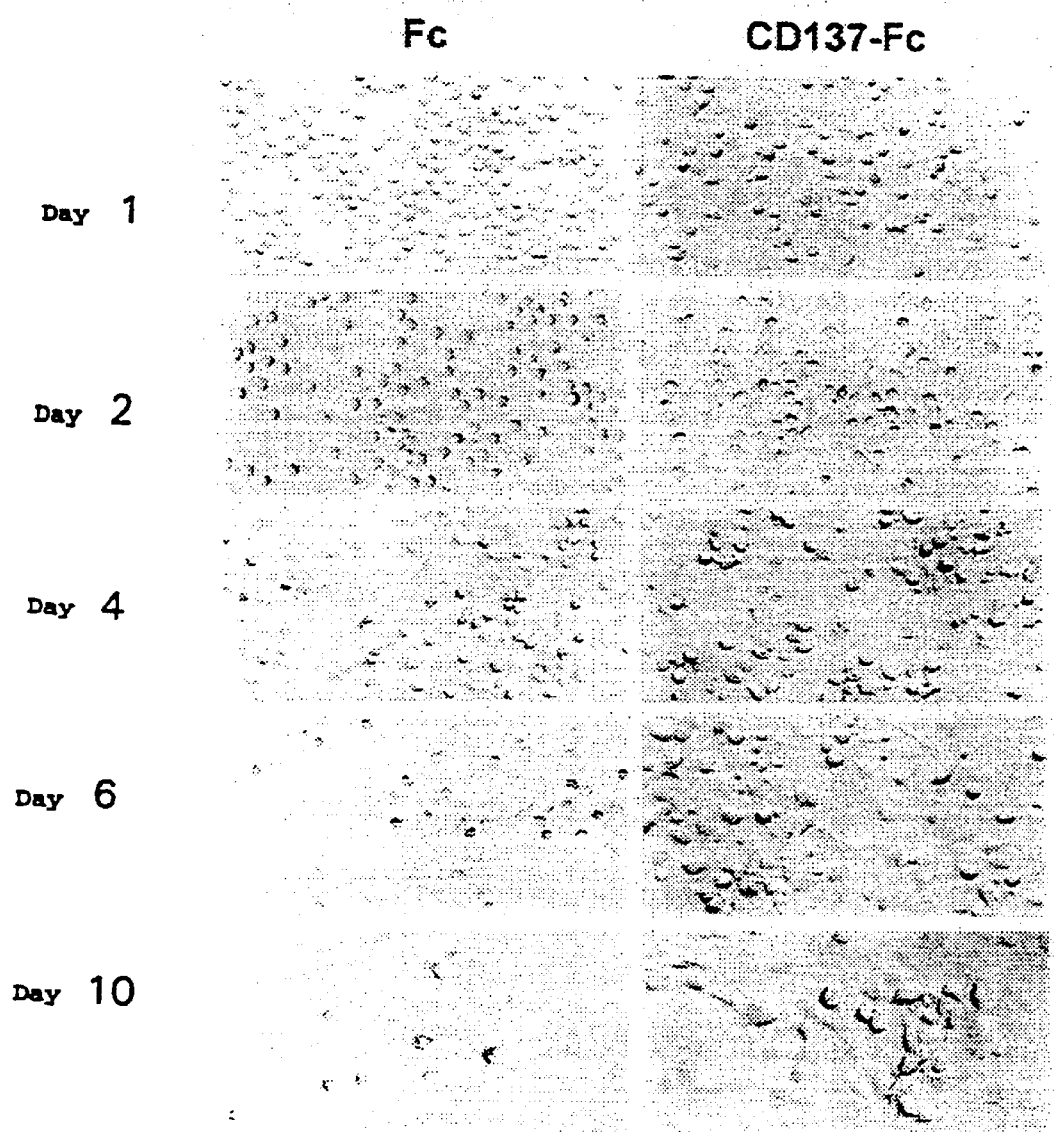
FIG. 9 shows a photographic representation of peripheral monocytes (A) cultured over immobilized Fc or CD137-Fc, 400 times magnification; (B) after 10 day's culturing over immobilized CD137-Fc; 500 times magnification.

CD137-Fc Induces Morphological Changes in the Monocytes $10^5$ primary peripheral monocytes were cultured on untreated tissue culture plates or over immobilized Fc or CD137-Fc protein (1 μg/ml). The cultures were photographed on day 1, 2, 4, 6 and 10 at 400 times magnification (FIG. 9A). Culture plates which had only been treated with Fc protein only showed a slight adhesion of the monocytes. Moreover, the monocytes retained their round morphology. In the course of 10 days, the monocytes in this batch gradually died (FIG. 9A, left column). A completely different result is obtained, however, if the cells have been cultured on tissue culture plates on which CD137-Fc fusion protein had been immobilized. CD137-Fc induces an adhesion of the monocytes. These cells gradually assumed an irregular shape. This effect could already be observed on day 1. With an increasing culturing period, the cells spread, increased in size and showed a more complex morphology (FIG. 9A, right column).

Figure 9B:
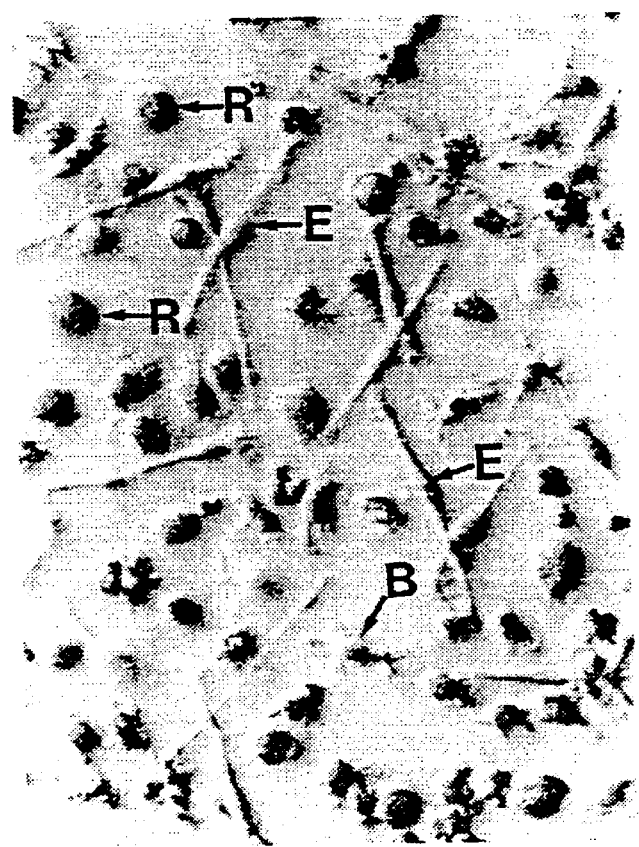

On day 10 of culturing in the presence of immobilized CD137-Fc, it was possible to identify three fundamental morphologies of monocytes differentiated in vitro: an elongated form (E), a round form (R) and a branched form (B) (cf. FIG. 9B).

Example 9

CD137-Fc Induces the Formation of M-CSF (a) $10^5$ primary monocytes were cultured in a first experiment over immobilized Fc or CD137-Fc (in each case 1 μg/ml). In order to keep CD137-Fc protein (1 μg/ml) in solution, in one batch the immobilization of CD137-Fc protein was prevented by preincubation of the tissue culture plates with foetal calf serum (1 h at 4° C., undiluted).

Figure 10:
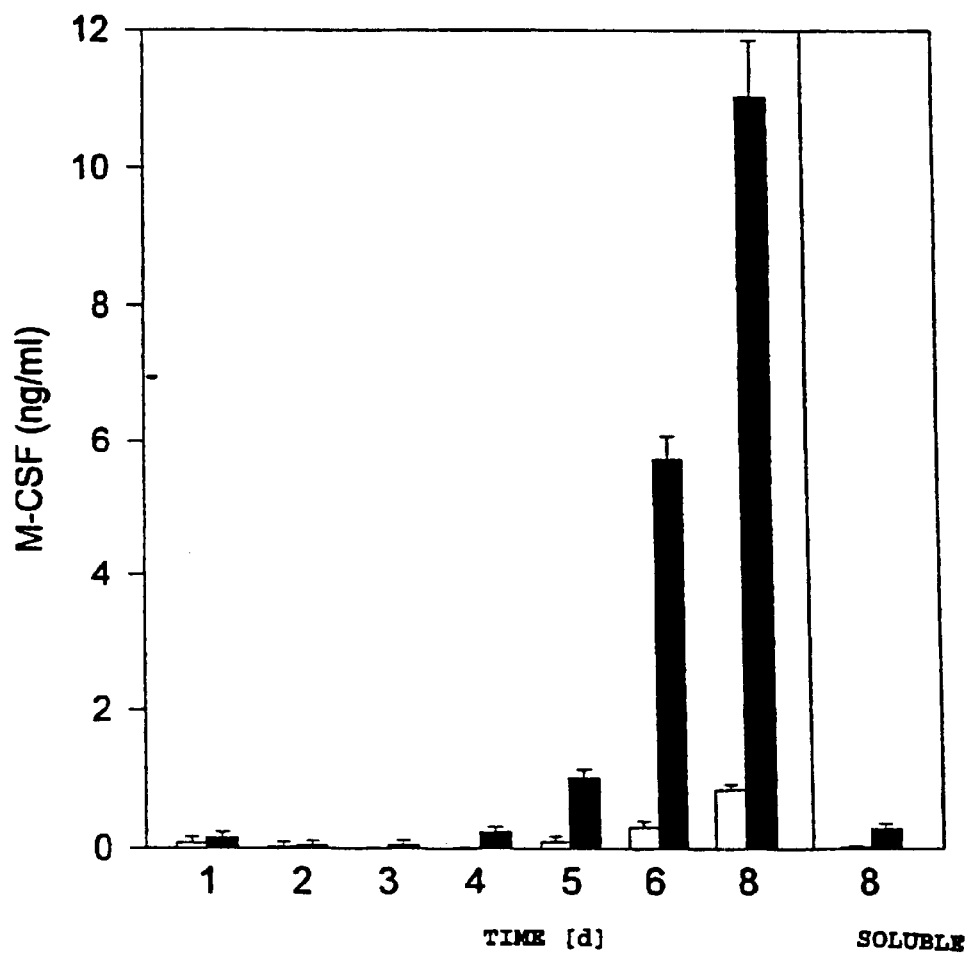
FIG. 10 shows in the left half of the graph the expression of M-CSF by monocytes after 1 to 8 day's culturing over immobilized Fc (white bars) or immobilized CD137-Fc (black bars); and in the right half of the graph the expression of M-CSF in the presence of soluble Fc or soluble CD137-Fc after 8 day's culturing.

The results are shown in FIG. 10. The culture supernatants were harvested at the times indicated and the M-CSF concentration was determined by means of ELISA. Comparable results were obtained in three separate experiments.

As FIG. 10 shows, CD137 induces the expression of M-CSF. During the first three days of culturing, the M-CSF contents were low and no difference was seen between the control and the CD137-treated monocytes. From day 4, the formation of M-CSF was detectable and the concentration of M-CSF increased rapidly and continuously. Immobilization of the CD137 protein was a necessary prerequisite for significant M-CSF formation, since soluble CD137 only induced low M-CSF concentrations.

Figure 11:
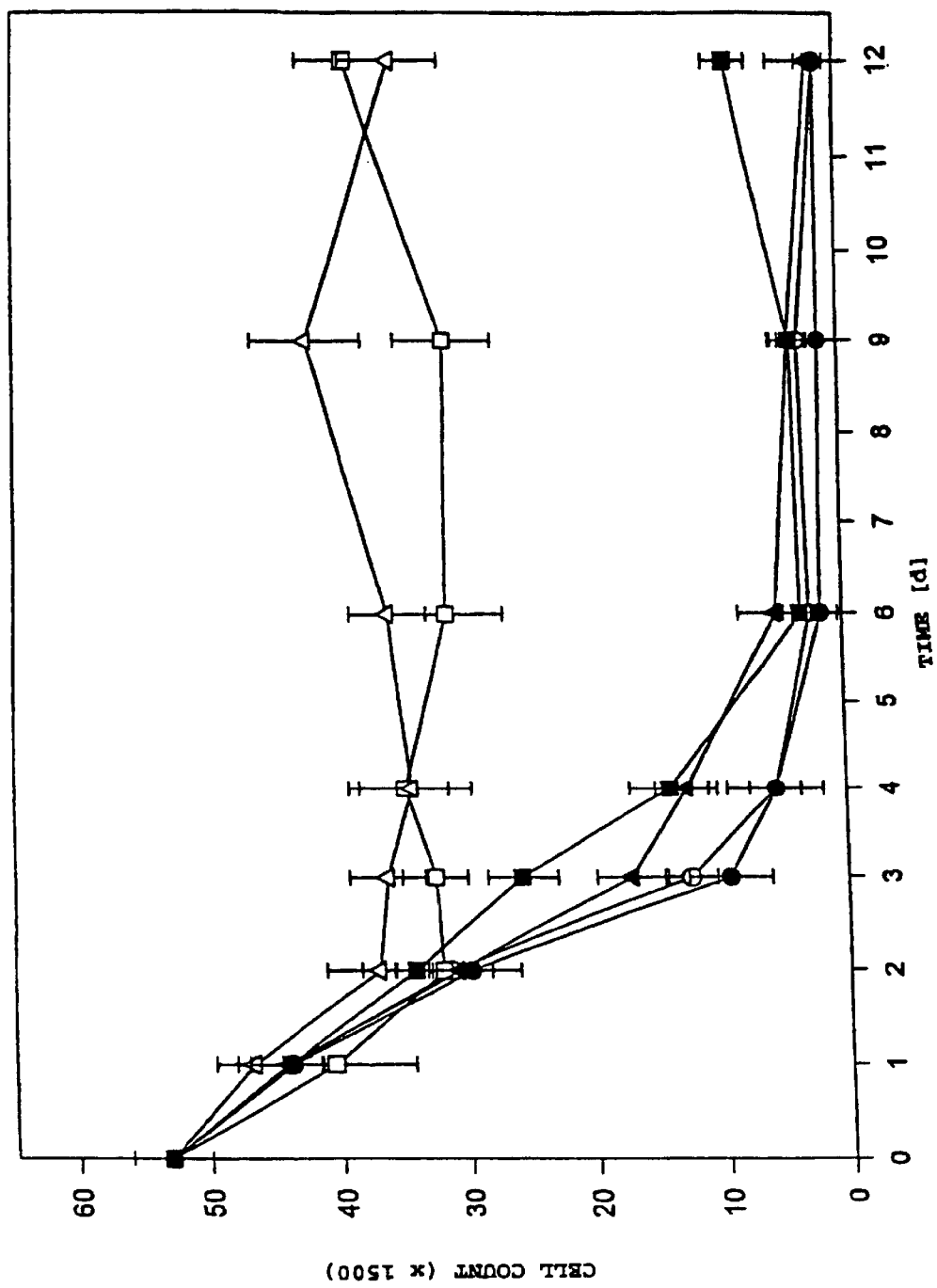
FIG. 11 shows the number of living monocytes after neutralization of M-CSF; the number of living monocytes treated with Fc (circle) or CD137-Fc (square) or with 100 ng/ml of M-CSF (triangle) without (light symbols) or after addition of 2 µg/ml of neutralizing anti-M-CSF antibody (black symbols) is indicated.

(b) In a next experiment, it was shown that the expression of M-CSF is not only induced by CD137, but is also essential for the survival of CD137-induced monocytes. For this, the monocytes were cultured in the presence of immobilized CD137 protein and neutralizing anti-M-CSF antibodies. It was observed that approximately ten times more monocytes survived on CD137-Fc-coated plates in comparison with Fc protein-coated plates. The addition of neutralizing anti-M-CSF antibodies lowered the number of surviving monocytes to the base value (cf. Table 1). On observation of the time course, it was found that the majority of the cultured cells on uncoated or Fc-coated cultured plates were already dead on day 6 (cf. FIG. 11). Immobilized CD137 protein or M-CSF, however, stabilized the cell count at a high level even on day 12. After capturing M-CSF with the aid of neutralizing antibodies, this effect was no longer observed.

It is known that in addition to M-CSF, GM-CSF and IL-3 in man also positively affect the lifetime of monocytes. It was not possible to find any expression of GM-CSF or IL-3 in the ELISA after culturing for 8 days (in the control batch and in CD137-treated cells) in the experiments according to the invention (results not shown). Neutralizing anti-GM-CSF antibodies, however, decreased the CD137-mediated monocyte survival rate by a half (cf. Table 1). Anti-Il-3 antibodies had no effect. A combination of neutralizing anti-IL-3 antibodies and anti-GM-CSF antibodies, however, lowered the number of surviving monocytes nearly to the base value. This shows that IL-3 also has an important role for the survival of the monocytes. Neutralization of GM-CSF and/or IL-3 additionally to the neutralization of M-CSF leads to no further lowering of the cell count.

It was possible to decrease the positive effect of M-CSF completely by administration of neutralizing anti-M-CSF antibodies and nearly to the base value by a combination of anti-GM-CSF and anti-IL-3 antibodies.

TABLE 1

| Stimulus | Neutralizing antibody[2] | Number of surviving cells[1] | p value[4] |
|---|---|---|---|
| Fc | — | 6.8 ± 1.5 | — |
| CD137-Fc | — | 75.5 ± 6.8 | — |
| CD137-Fc | α-M-CSF | 9.3 ± 2.0 | 0.005 |
| CD137-Fc | α-IL-3 | 72.3 ± 8.4 | n.s. |
| CD137-Fc | α-GM-CSF | 36.0 ± 2.5 | 0.006 |
| CD137-Fc | α-M-CSF + α-IL-3 | 7.0 ± 1.8 | 0.005 |
| CD137-Fc | α-M-CSF + α-GM-CSF | 6.0 ± 3.0 | 0.007 |
| CD137-Fc | α-GM-CSF + α-IL-3 | 19.0 ± 3.0 | 0.005 |
| CD137-Fc | α-GM-CSF + α-GM-CSF + α-IL-3 | 4.8 ± 3.3 | 0.008 |
| M-CSF | — | 68.3 ± 16.2 | — |
| M-CSF | α-M-CSF | 5.3 ± 2.6 | 0.006 |
| M-CSF | α-GM-CSF + α-IL-3 | 20.8 ± 5.0 | 0.018 |

Example 10

Immobilization of CD137 Protein Increases the Number of Live Monocytes $10^5$ peripheral monocytes were cultured on immobilized Fc or CD137-Fc protein (in each case 1 μg/ml) or in the presence of soluble FC or soluble CD137-FC protein (in each case 1 μg/ml). The cultures were photographed on day 8 at 300 times magnification (cf. FIG. 12). Immobilization was carried out by pretreatment of the culture plates with bovine serum albumin (30 min room temperature, 200 μl per well of a 96-hole plate). In the presence of soluble protein, the monocyte count is markedly lowered. In agreement with this finding, M-CSF is only induced if CD137 protein is present in immobilized form (cf. Example 9). It is therefore probable that CD137 only acts on monocytes when a CD137 ligand expressed by the monocytes (i.e. a binding partner for CD137) is crosslinked by means of the binding of immobilized CD137 molecules.

Soluble CD137-Fc which is secondarily crosslinked by means of anti-Fc antibodies likewise prolongs the survival of monocytes, observed after culturing for 8 days (results not shown). For this experiment, CD137-Fc (2 μg/ml) had been treated beforehand with goat anti-human Fc antibody (2 μg/ml).

What is claimed is:

1. A method for promoting proliferation of peripheral mononuclear cells in mammals comprising contacting said peripheral mononuclear cells with an effective amount of immobilized or aggregated CD137 under suitable conditions, thereby promoting the proliferation of peripheral mononuclear cells.

2. The method of claim 1, wherein the peripheral mononuclear cells are contacted with CD137 in vivo.

3. The method of claim 1, wherein the peripheral mononuclear cells are contacted with CD137 ex vivo.

4. The method of claim 1, wherein the promotion of proliferation of mononuclear cells further comprises contacting at least one additional factor selected from the group consisting of interleukins, lymphokines, monokines, interferons, colony-stimulating factors, leukocyte-stimulating factors and growth factors.

5. The method of claim 4, wherein the additional factor is a leukocyte-stimulating factor.

6. The method of claim 1, wherein the leukocyte-stimulating factor is selected from the group consisting of G-CSF, GM-CSF and M-CSF.

7. The method of claim 1, wherein the CD137 aggregate is a multimeric aggregate.

8. The method of claim 1, wherein the CD137 multimeric aggregate comprises 2 to 5 CD137 molecules.

9. The method of claim 1, wherein the CD137 comprises amino acids +18 to +186 of FIG. 1A (SEQ ID NO: 2).

10. A method of promoting the proliferation of peripheral mononuclear cells in a patient, comprising administering an effective amount of immobilized or multimeric aggregate of CD137 to the patient.

11. The method of claim 10, wherein the patient has a decreased number of active peripheral mononuclear cells compared to normal.

12. The method of claim 10, wherein the patient has a depressed immune response compared to normal.

13. The method of claim 10, wherein the patient has damage to the haematopoietic system resulting from chemotherapy or radiation therapy.

14. The method of claim 10, wherein the patient has a wound healing disorder.

15. The method of claim 10, wherein the patient is suffering from oncoses.

16. The method of claim 10, wherein the patient has a bacterial, viral or fungal infection.

17. The method of claim 10, wherein the patient has an inherited or non-inherited, acquired or non-acquired immune system condition.

18. The method of claim 10, wherein the patient is being treated with immunosuppressants.

19. The method of claim 10, wherein CD137 is administered in vivo.

20. The method of claim 10, wherein CD137 is administered ex vivo.

21. The method of claim 10, wherein the method further comprises administering at least one additional factor selected from the group consisting of interleukins, lymphokes, monokines, interferons, colony-stimulating factors, leukocyte-stimulating factors and growth factors.

22. The method of claim 21, wherein the additional factor is leukocyte-stimulating factor.

23. The method of claim 22, wherein the leukocyte-stimulating factor is selected from the group consisting of G-CSF, GM-CSF and M-CSF.

24. The method of claim 10, wherein the CD137 aggregate is a multimeric aggregate.

25. The method of claim 23, wherein the CD137 multimeric aggregate comprises 2 to 5 CD137 molecules.

26. The method of claim 10, wherein the CD137 comprises amino acids +18 to +186 of FIG. 1A (SEQ ID NO: 2).

27. A method of promoting the proliferation or growth of peripheral mononuclear cells from the blood of mammals in vitro comprising contacting said peripheral mononuclear cells with an effective amount of immobilized or aggregated CD137 in a nutrient medium and incubating said peripheral mononuclear cells with said CD137 until the peripheral mononuclear cells proliferate or grow.

28. A method of promoting the proliferation of peripheral mononuclear cells in chemotherapy and radiation therapy comprising:
   a) collecting a blood sample containing peripheral mononuclear cells from said patients prior to the chemotherapy or radiation therapy;
   b) incubating said blood sample ex vivo with an effective amount of immobilized or aggregated CD137; and
   c) administering the treated blood fraction to the patient after completion of the chemotherapy or radiation therapy thereby promoting the proliferation of peripheral mononuclear cells.

29. A method of promoting the proliferation of peripheral mononuclear cells in chemotherapy and radiation therapy patients comprising administering an effective amount of immobilized or aggregated CD137 to the patient, thereby promoting the proliferation of the endogenous peripheral mononuclear cells.

30. The method of any of claims 27, 28, or 29, wherein the CD137 aggregate is a multimeric aggregate.

31. The method of claim 30, wherein the multimeric aggregate comprises 2 to 5 CD137 molecules.

32. The method of any of claims 27, 28, or 29, wherein the CD137 has an extracellular portion corresponding to amino acids +18 to +186 of FIG. 1A1 (SEQ ID NO: 2).

* * * * *